US007295889B2

United States Patent
Lähteenmäki

(10) Patent No.: US 7,295,889 B2
(45) Date of Patent: Nov. 13, 2007

(54) NUTRITION DISPENSERS AND METHOD FOR PRODUCING OPTIMAL DOSE OF NUTRITION WITH THE HELP OF A DATABASE ARRANGEMENT

(76) Inventor: Pertti Lähteenmäki, Parkkikuja 7, Helsinki (FI) FI-00850

( * ) Notice: Subject to any disclaimer, the term of this patent is extended or adjusted under 35 U.S.C. 154(b) by 170 days.

(21) Appl. No.: 10/499,988

(22) PCT Filed: Dec. 23, 2002

(86) PCT No.: PCT/FI02/01056

§ 371 (c)(1), (2), (4) Date: Nov. 12, 2004

(87) PCT Pub. No.: WO03/056493

PCT Pub. Date: Jul. 10, 2003

(65) Prior Publication Data

US 2005/0048461 A1    Mar. 3, 2005

(30) Foreign Application Priority Data

Dec. 28, 2001  (FI)  ................................. 20012593
May 31, 2002  (FI)  ................................. 20021031

(51) Int. Cl.
*G06F 17/00*    (2006.01)
(52) U.S. Cl. ........................ 700/233; 700/239; 700/240
(58) Field of Classification Search ................ 700/233, 700/237, 236, 239, 240, 242, 241; 435/3
See application file for complete search history.

(56) References Cited

U.S. PATENT DOCUMENTS 5,233,520 A  8/1993  Kretsch et al.
5,299,529 A  4/1994  Ramirez
5,390,238 A * 2/1995  Kirk et al. .............. 379/106.02
5,412,564 A  5/1995  Ecer (Continued)

FOREIGN PATENT DOCUMENTS

EP  0 427 875  5/1991

(Continued)

OTHER PUBLICATIONS de Kleer, J., An assumption-based TMS, Journal of Artificial Intelligence 28 127-162 1986.

(Continued)

*Primary Examiner*—Gene O. Crawford
*Assistant Examiner*—Timothy Waggoner
(74) *Attorney, Agent, or Firm*—Young & Thompson

(57) ABSTRACT

A nutrition dispenser (100) for producing doses of nutrition and/or medication and a method for producing the doses with the help of the nutrition dispenser. A database arrangement is linked to the nutrition dispenser (100), and further, the nutrition dispenser typically includes the user interface (102) for feeding at least the information of the user, and rooms (108) for storing different nutrients and/or medical substances. In addition, the nutrition dispenser is arranged to define the optimal dose of nutrition and/or medication intended for the person consuming the dose, and its ingredients, amounts and proportions of ingredients at least partly with the help of the database arrangement. The nutrition dispenser can further comprise the equipment (110) for measuring out the defined nutrients.

20 Claims, 5 Drawing Sheets

U.S. PATENT DOCUMENTS

| | | | |
|---|---|---|---|
| 5,672,154 A * | 9/1997 | Sillen et al. ............... | 604/503 |
| 5,704,350 A | 1/1998 | Williams, III | |
| 5,853,244 A * | 12/1998 | Hoff et al. ............... | 366/141 |
| 5,985,559 A | 11/1999 | Brown | |
| 6,000,828 A | 12/1999 | Leet | |
| 6,024,281 A | 2/2000 | Shepley | |
| 6,039,688 A | 3/2000 | Douglas et al. | |
| 6,283,914 B1 | 9/2001 | Mansfieldl et al. | |
| 6,304,797 B1 | 10/2001 | Shusterman | |
| 6,321,641 B1 | 11/2001 | Wang | |
| 6,335,907 B1 * | 1/2002 | Momich et al. ............ | 368/10 |
| 6,696,924 B1 * | 2/2004 | Socinski ................... | 700/233 |
| 6,746,371 B1 * | 6/2004 | Brown et al. ............. | 482/8 |
| 2002/0082869 A1 | 6/2002 | Anderson | |

FOREIGN PATENT DOCUMENTS

| | | |
|---|---|---|
| JP | 07271857 | 10/1995 |
| WO | WO 00/41575 | 7/2000 |
| WO | WO 00/51053 | 8/2000 |
| WO | WO 01/95230 | 12/2001 |
| WO | WO 02/37398 | 5/2002 |

OTHER PUBLICATIONS

Dempster, A., Upper and lower probabilities induced by a multivalued mapping, Anneals of Mathematical Statistics 38 325-339 1967.

Kowalski, R., Predicate logic as a programming language, Proceedings of IFIP 74 569-574 North Holland Publishing Company 1974.

Shafer, G., A Mathematical Theory of Evidence, Princeton University Press 1976 35-273.

* cited by examiner

NUTRITION DISPENSERS AND METHOD FOR PRODUCING OPTIMAL DOSE OF NUTRITION WITH THE HELP OF A DATABASE ARRANGEMENT

The invention relates to a nutrition dispenser. More specifically, the invention relates to a nutrition dispenser producing doses of nutrition and/or medication to the user, and to a system and method for the production of doses of nutrition and/or medication to the user with the help of the said nutrition dispenser.

In the past decades, the average life expectancy of human beings has grown considerably because of the advanced medical methods of treatment. At the same time, new diseases and illnesses have come out, such as different kinds of allergies, especially to foodstuffs. In addition, obesity has become common especially in developed countries, in which the daily motion of humans has continuously decreased, for example, due to work performed by humans becoming lighter and due to automation. At the same time, humans' eating habits have changed, for example, as socalled fast-food restaurants have become more common. Nowadays, the busy way of life and the number of people living alone in relation to previous times have further increased so that more and more people resort to foods offered by fast-food restaurants, to ready-prepared products that can be consumed fast, or to products to be bought from separate food vending machines, such as rolls and soft drinks.

Although specific special foodstuffs and health foods are now in good supply, nevertheless, the major part of people eats in an unhealthy or unsuitable way, for example, in relation to the energy consumption, illness or latent illness, and does not think about the nutrients contained in the nutrition consumed or the effects on their health. The significance of nutrients contained in the nutrition frequently consumed, for example, in the generation and progress of illnesses is not even realised, and staying healthy is considered obvious.

However, the consumed nutrition plays an important role in the generation and progress of almost all illnesses. Especially for persons following a special diet, such as sportsmen, weight-watchers, allergic persons, pregnant women, diabetics, and persons suffering from illnesses, and persons otherwise taking care of their health, the additives and nutrients contained in the nutrition, and their amounts and/or proportions are especially important for the optimal result, for increasing or maintaining physical fitness, for staying healthy and/or for preventing the worsening of an illness. However, it has to be noted that also healthy persons should watch the quality, amounts and proportions of nutrients contained in the nutrition they consume in order to stay healthy, fit for work and vital.

However, monitoring the nutrients contained in the consumed nutrition is often considered difficult or laborious, and it is only thought to be relevant mostly for persons following a special diet for one reason or another. In some cases, it may also be difficult for people to monitor the nutrient contents in the consumed food and/or drink or other substances contained in foods and medicaments, which may, for example, cause illnesses or make allergies worse. For example, people may have difficulties in remembering or generally in knowing all nutrients harmful for them, in which case, for example when shopping, it may be difficult for a person to know the suitability of a certain product for him. Especially, if one thinks of the overall effect of nutrients acquired in one day or even one week, it is almost impossible to find out the suitability, goodness and/or effect of a certain foodstuff in relation to the overall effect of nutrients obtained in one day or one week. Further, a high threshold to just the user in question in the manufacture of optimal nutrition is often to find suitable nutrients and optimise them in relation to other substances and to the user's condition, and also the manufacturing process of the nutrition in itself. The manufacturing process of nutrition is easily thought to be a too time-consuming and sometimes even frustrating, messy and complicated or unpleasant process.

However, some solutions are previously known for monitoring the supply of nutrients of a person, for example, during a diet or weight watching. For example, the publication U.S. Pat. No. 5,412,564 presents a solution, in which the consumption of nutrition of a consumer can be monitored and information concerning the consumption of nutrition can be stored. The publication U.S. Pat. No. 5,233,520 again discloses a solution for an interactive, computerised measuring apparatus of nutrition, which can be used for measuring the food, nutrients and other food components consumed by the person. Further, solutions are known from the state-of-the-art technology also for manufacturing a prepared dose of nutrition, for example, different kinds of baking machines (e.g. U.S. Pat. No. 6,321,641), to which appropriate amounts of ingredients needed in the baking of bread are placed in advance, and the baking machine can then mix the ingredients at a predetermined moment and make the bread. In addition, a solution for offering a dose of nutrition is known, among others, from the publication U.S. Pat. No. 5,299,529, in which the size of doses of nutrition to be served and the time of serving can be determined in advance.

However, it is not possible to fully eliminate the above disclosed problems for automatically manufacturing and serving fast a dose of nutrition and/or medication optimised for the user with the arrangements of the known solutions so that, for example, the user's health and physical condition, the user's possible allergies and restrictions, and the information about the nutrients and/or medical substances consumed by the user and the energy consumption could be taken into account.

The object of the invention is to create a solution for a nutrition dispenser so that the said drawbacks related to the state-of-the-art technology can be reduced. The invention aims to solve how a dose of nutrition and/or medication best suited for the user in relation to the user's characteristics, such as his physical condition and energy consumption, can be prepared automatically, fast, easily and cost-effectively. In addition, it is the object of the invention to make possible a solution, with the help of which an individualised and optimal dose of nutrition and metabolic state and possible medication can be personified for the user, taking into account the user's genotype, possible illnesses and medication and environmental conditions.

The objects of the invention are achieved by an arrangement, in which information concerning the user's condition are analysed in relation to information obtained from medical and biological researches for identifying nutrition optimal for the user, and the nutrients for achieving the optimal dose of nutrition and/or medication are defined from the library of nutrients fed to the system at least partly with the help of neurofuzzy systems and methods. Further, the objects of the invention are achieved by arranging the said arrangement to a nutrition dispenser, which further comprises nutrients and/or medical substances needed in the manufacturing of a dose of nutrition and/or medication, a dosing device and a mixer.

It is characteristic of the nutrition dispenser of the invention for producing a dose of nutrition and/or medication that the nutrition dispenser is provided with a database arrangement, that the nutrition dispenser comprises a user interface for feeding at least information related to the user, rooms for storing at least two nutrients and/or medical substances, and that the nutrition dispenser is arranged to define an optimal dose of nutrition and/or medication to the person consuming the dose, and the ingredients, quantities and proportions of ingredients at least partly with the help of the said database arrangement, and that the nutrition dispenser comprises means for measuring out the defined nutrients and/or medical substances.

The system of the invention for producing a dose of nutrition and/or medication is characterised in that a database arrangement is connected to the system, that the system comprises a user interface for feeding at least information related to the user, room for storing at least two nutrients and/or medical substances, and that the system is arranged to define an optimal dose of nutrition and/or medication intended for the person consuming the dose, and the ingredients in the dose, the quantities and proportions of the ingredients at least partly with the help of the said database arrangement, and that the arrangement comprises means for measuring out the defined nutrients and/or medical substances.

It is characteristic of the method of the invention for producing a dose of nutrition and/or medication with the help of a nutrition dispenser that, in the method, at least information related to the user are fed to the nutrition dispenser, an optimal dose of nutrition and/or medication is defined for the person consuming the dose, and the ingredients in the dose, the quantities and proportions at least partly with the help of the database arrangement, and the defined nutrients and/or medical substances are measured out.

Some advantageous embodiments of the invention are disclosed in the dependent patent claims.

Among others, the following concepts are used in this patent application:

"User" is any individual or group of individuals, which can use the nutrition dispenser of the invention. Especially, the user is a person consuming the dose of nutrition and/or medication, the information on the state of health and genetic background of which considered sufficient for the system can be delivered to the system, and the nutrition information on the product consumed or ordered or intended to be consumed by which can be delivered to the system possibly used by the nutrition dispenser for identifying the nutrition optimal for the user. In addition, user is any individual or group of individuals, to which optimal nutrition information identified by the nutrition information service of the invention can be delivered. The user can be a human being or an animal or a larger entity formed of these, for example, a sports team engaging in a certain sport.

"Nutrient and/or medical substance" is a substance significant for the relation between nutrition and an illness. A nutrient and/or medical substance can typically be, for example, a water-soluble or lipo-soluble vitamin, protein, micro-nutrient, carbohydrate, amino acid, unsaturated or saturated fat, mineral, soluble or insoluble fibre, flavonoid, other phospholipid or phenolic substance or plant estrogen. In this connection, nutrient can also be understood to comprise harmful substances, such as environmental estrogens. Further, in this connection, nutrient can also be understood to comprise medicaments, bacteria, such as the lactobacillus group, or some other microbe and water.

"Nutrition information" is information representing the nutritive contents of a foodstuff, food product or medicament and/or its suitability for a user.

"Dose of nutrition and/or medication", foodstuff, food product, product or food is any product comprising one or several nutrients and/or medical substances fit or unfit to be consumed, such as a food portion, drink, mixture or medicament, or a combination of these. A dose of nutrition and/or medication is typically a dose of nutrition suggested and/or prepared by the nutrition dispenser of the invention. Respectively, foodstuff refers to a product consumed by the user, for example, fish and, more specifically, pike. In this application, foodstuff can also comprise hygienic products, such as washing agents and chemicals, for example, shampoos, make-ups and suntan creams. The dose of nutrition can also be a dose consisting merely of medical substances; for example, a dose defined for a certain patient.

"Reference information" is information concerning a reference group, such as information representing relations between health, physical performance and/or food habits characteristic of the said group. The reference group can, for example, be a tribe, race or nationality, or some population group, sports group, or profession. The smallest element in a reference group can be an individual.

"Intake limit" is an intake limit comprising the upper and lower limit, defined for a certain nutrient and/or medical substance for a certain time period; for example, with salt, the daily intake limit can be 1-5 g. Also a time limit is typically connected with the intake limit, within which the nutrient and/or medical substance related to the intake limit should be obtained in an amount which is within the area defined by the lower and upper limits of the intake limit.

"Health property" is a psycho-physical condition, such as an illness. The health property can also comprise information, for example, about the user's energy consumption and need.

"Scientific research information" is information obtained from scientific researches, such as biological, medical and psychological researches. In this application, scientific research information especially refers to information about genetics, properties determined by genes, functionality of genes, and connections between different foodstuffs and illnesses, obtained from biological and medical researches. In its minimum, scientific research information comprises information about the genetic backgrounds of different illnesses in relation to nutrition and environmental factors and the effective agents in at least one medicament. Most preferably, in the system of the invention, the said scientific research information is in a processed form so that, for example, a certain probability has been formed between different genes and illnesses, to which the said gene exposes, with which the said gene causes the said illness. Scientific research information can also be information about what illnesses and/or symptoms certain substances cause either to all people or, for example, to a certain group of people, such as tribes, races or even families or individuals with a certain probability. For example, the information can comprise information that obesity and western nutrition cause diabetes with a certain probability, cholesterol and salt cause cardiac and vascular disease and osteoporosis, western nutrition causes allergies and asthma, environmental estrogens and western nutrition cause hormone-dependent cancers, carcinogens cause the cancer of the colon, fibres protect from the cancer of the colon, and that some infections cause a certain type of rheumatism.

Considerable advantages are achieved with the present invention compared with state-of-the-art solutions. The invention makes it possible to prepare a dose of nutrition and/or medication personified for the user fast, automatically and cost-effectively, without the user having to take considerable measures for the actual manufacturing process. In addition, the method of the invention makes possible the utilisation of medical and biological research information and of the information describing the user's environmental conditions, physical load, energy consumption, genetic properties, possible illnesses and nutrient limitations caused by these when defining and manufacturing an individualised dose of nutrition and/or medication optimal for the user with the help of the nutrition dispenser of the invention.

With the help of the nutrition dispenser of the invention, also information about the quality and quantity of the nutrients consumed by the user can be maintained in the database arrangement of the information system, with which the nutrition dispenser of the invention can be in data transmission connection. Alternatively, at least part of the information system and its database arrangement can be integrated to the nutrition dispenser. In addition, the database arrangement makes it possible for the user and/or the medical personnel treating the user to observe the quantities and proportions of the nutrients, additives, medical substances and other respective substances daily obtained by the user, and also the deficiencies of some substances in real time. With the help of the nutrition dispenser of the invention, it is also possible to take into account in real time nutrient, medication and research information concerning the user and/or other general nutrient, medication and research information and probability weighting coefficients defined to the database arrangement by the medical personnel or some other authorised organ, with which a certain nutrient and/or medical substance exposes to a certain illness, and the intake limits for nutrients and/or medical substances within a certain period, such as NaCl 1-5 g/24 h.

At its simplest, the nutrition dispenser according to the invention can be realised by providing the nutrition dispenser with a user interface, such as a keyboard, with which the user can feed information to the nutrition dispenser, for example, about his gender and age, and possibly information about the need or consumption of energy at a certain time. In addition, at its simplest, the nutrition dispenser can be equipped with rooms, such as separate containers or storages, in which substances required for a dose of nutrition and/or medication optimised for the user can be separately stored. The nutrition dispenser can further be provided with equipment, such as an information arrangement or its part and a related information unit, with the help of which nutrients and/or medical substances, their amounts and proportions suitable for the user are defined in relation to the information fed by the user, with a dosing device, with which suitable amounts of the defined substances are measured out, and with a mixer, with which the defined substances are mixed to a form to be consumed by the user.

Nutrients and/or medical substances can be, for example, semifinished products, processed products, synthetically manufactured substances, or combinations of these, such as blueberry, compressed blueberry, blueberry juice, antocyane separated from blueberry, synthetically manufactured antocyane, or a combination of these. Substances in the nutrition dispenser can, for example, be in form of a liquid, concentrate or powder, an emulsion, tablet, effervescent tablet, capsule, pill, granule or pieces of ice; however, most preferably in a form to be easily mixed with water.

Besides water and flavour substances, nutrients can further comprise, for example, medical substances, amino acids, carnitine, taurine, nucleotides, choline, inocitol, fibres, flavonoids, such as pygnogenols, isoflavonoids, such as formononetin, lignane, aminoacids, proteins, minerals and micronutrients, such as magnesium, potassium or chrome, lycopen, fibres, carbohydrates, such as glucose and fructose, salts, fats, minerals, substances containing scents, components of green tea, such as catechin and/or epicatechin, caffeine, guarana, green tea extract, pygnogenol, betaine, methyl sulphonyl methane (MSM), magnesium, potassium, chrome, carnitine, taurine, peptides, amino acids, such as taurine chonroitin sulphate, mucopolysaccharides, such as chonroitin sulphate, glucosamino glycan, curcuma, alpha-lipoin acid, antibodies, colostrums preparation, probiotics, prebiotics, herbs, such as maidenhair tree (*Ginkgo biloba*), passion flower (*Passiflora incarnata*), milk thistle (*Carduus marianum*), hop, oat sprout, lemon balm and ethereal oils, such as aniseed, nutmeg or cinnamon, adaptogenic plant extracts, such as roseroot (*Rhodiola rosea*), ginseng, Russian root (*Acanthopanax senticosus*), and maral root (*Leuzea carthamoides*), vitamins, such as vitamin C and vitamins of the group B; carotenoids, garlic preparation, secoiridoids, soluble fibres, fatty acid and phospholipids.

Vitamins can be, for example, vitamins A, D, E, K, B1, B2, B6, B12, and C, retinol, retinyl acetate, retinyl palmitate, beta-carotene, cholecalcipherol, ergocalcipherol, D-alpha-tocopherol, DL-alpha-tocopherol, D-alpha-tocopheryl acetate, D-alpha-tocopheryl acid succinate, phyllochinone, thiamine hydrochloride, thiamine mononitrate, riboflavin, sodium riboflavin-5'-phospate, nicotine acid, nicotine amide, calcium-D-pantotenate, natrium-d-pantotenate, dexpanthenol, pyridoxine hydrochloride, pyridoxine-5'-phosphate, pyridoxine dipalmitate, pteroyl-monoglutamin acid, cyan-cobalamin, hydroxo-cobalamin, D-biotin, L-ascorbin acid, sodium-L-ascorbate, calcium-L-ascorbate, potassium-L-ascorbate, and L-ascorbyl-6-palmitate.

Minerals can be, for example, calcium, magnesium, iron, copper, iodide, zinc, mangane, sodium, potassium, selenium, chrome (III) and hexahydrates, molybden, fluoride, carbonate, chloride, salts of lemon acid, gluconate, glycerophosphate, lactate, salts of ortophosphoric acid, hydroxides, oxides, acetate, sulphate, ferrocarbonates, ferrocitrates, ferriammoniumcitrate, ferrogluconate, ferrofumarate, ferrisodiumdi-phosphate, ferrolactate, ferrosulphate, ferridiphosphate, ferrisaccharate, iron in form of elements, copper carbonate, copper citrate, copper gluconate, copper sulphate, copper-lycine complex, potassium iodide, potassium iodate, sodium iodide, sodium iodate, bicarbonates, sodium celenate, sodium -hydro-celenite, sodium celenite, ammonium molybdate, sodium molybdate, potassium fluoride, and sodium fluoride.

Amino acids can be, for example, L-alatine, L-arginine, L-cystene, L-cystine, L-histidine, L-glutamine acid, L-glutamine, L-isoleucine, L-leucine, L-lycine, L-lycine acetate, L-metionine, L-ornitine, phenylalanine, L-treonine, L-tryptophane, L-tyrocine, and L-valine.

Carnitines and taurines can be, for example, L-carnitine, L-carnitine hydrochloride, and taurine.

Nucleotides can be, for example, adenocine-5'-phosphoric acid (AMP), sodium salts of AMP, cytidine-5'-monophosphoric acid (CMP), sodium salts of CMP, guanocine-5'- phosphoric acid (GMP), sodium salts of GMP, inocine-5'-phosphoric acid (IMP), sodium salts of IMP, uridine-5'-phosphoric acid (UMP), and sodium salts of UMP.

Cholines and inocitols can be, for example, choline, choline-chloride, cholonbitartrate, choline-citrate, and inocol.

Amino acids can be, for example, L-asparagine acid, L-citrulin, glycine, and L-proline.

Further, the dose of nutrition and/or medication to be manufactured with the nutrition dispenser of the invention can be, for example, a drink composition, which can contain medical substances, for example, medical substances influencing blood pressure, asthma, allergy or the well-being of the skin.

The nutrition dispenser of the invention includes considerable advantages. When using separate rooms, substances that easily go bad with other substances can be kept in own rooms in conditions that are advantageous for the substances in question. Nutrients and/or medical substances to be mixed can be, for example, substances that are not preserved in water phase, but which are preserved dry. Such a substance is, for example, lycopen. In addition, flavonoids among others decompose when exposed to sunlight, in which case such substances can be kept in a room of the nutrition dispenser protecting from sunlight. Cleaner doses can be achieved with the nutrition dispenser, because when using the optimal rooms of the nutrition dispenser, no preservatives need necessarily be added to the substances at all, or at least to a considerably lesser extent than typically.

The operation of the nutrition dispenser is substantially based on the utilisation of the information system and the database arrangement in it. With the information system it is possible to analyse, among others, information about the user's genetic properties, possible illnesses, environmental conditions and/or consumed nutrition in relation to information obtained from medical and biological researches for identifying nutrition optimal for the user. With the information system, suitable nutrients and/or medical substances for preparing an optimal individualised dose of nutrition and/or medication can be defined by utilising at least partly learning neurofuzzy systems and methods.

Besides the information mentioned above, the database arrangement of the information system can also comprise reference information, scientific research information and information related to the user, such as, information about the user's age, gender, weight, length, genetic background and structure, genotype (DNA), functional state of genes, tribe, group, nationality, illnesses, allergies, mental state, medication, living environment, working environment, type of work, family relations, individual history, and work or sports performance. Information concerning the user can also be a value or information about the fat percentage, blood pressure, blood sugar, hemoglobin and/or cholesterol. Most preferably, the information is in a processed form in the database arrangement, for example, as probabilities that a certain nutrient and/or medical substance exposes to or protects from a certain illness with a certain probability when taken as doses of a certain size.

Preferably information related to the user is a sufficient piece of information about the user's genetics, functionality of genes and/or physiological characteristics, on the basis of which the user's nutritive and medical basic needs can be determined. With the help of information related to the user, also the limitations caused by illnesses can be taken into account and found out for the manufacturing process of a dose of nutrition to be manufactured for the user, or for the preparation, planning and realisation of medication intended for the user. Information can also be information about the user's diseases of the locomotor system, depression, cardiac disease, hypertension, allergy, asthma, headache, migraine, mental illness, illnesses caused by alcohol, dementia and hormone-dependent cancer.

The database arrangement can especially comprise at least one probability weighting coefficient for at least one gene influencing at least one health property with a certain probability, and for at least one nutrient and/or medical substance influencing at least one health property in a healing or harmful manner with a certain probability. In addition, the database arrangement can comprise at least one probability weighting coefficient for at least one gene influencing at least one health property with a certain probability, and at least one probability weighting coefficient for at least one nutrient and/or medical substance influencing at least one health property in a healing or harmful manner with a certain probability. Further, the database arrangement can comprise at least one probability weighting coefficient for at least one gene together with at least one nutrient and/or medical substance influencing at least one health property in a healing or harmful manner with a certain probability, and at least one probability weighting coefficient for the user to be allergic to at least one nutrient and/or medical substance with a certain probability. The database arrangement can further comprise information about the optimal quantity proportions of at least two nutrients and/or medical substances and the individualised intake limits for at least one nutrient and/or medical substance.

In addition, the database arrangement can preferably be arranged to form a notification to the nutrition dispenser, if the cumulative amount of the said nutrient and/or medical substance within a predetermined time period is either higher or lower than the individualised intake limit of the said nutrient and/or medical substance defined for the user, in which case the nutrition dispenser can either add the said nutrient and/or medical substance to the said dose, or to reduce its amount in the dose. In addition, the database arrangement can preferably be arranged to compare at least one gene from the user's genetic map with the genetic map information in the database arrangement, and to select the probability weighting coefficient between the said gene, which gene is both in the user's genetic map and in the database arrangement, and at least one health property, which the said gene influences, and further, to select the probability weighting coefficient between the said health property and at least one nutrient and/or medical substance, which influences the said health property either in a healing or harmful manner with a certain probability, and to form information describing the suitability of the said nutrient and/or medical substance for the user with the help of the said probability weighting coefficients. Especially the system can be arranged to arrange the nutrients and/or medical substances influencing the said health property in a healing or harmful manner with a certain probability and the probabilities related to the nutrients and/or medical substances that were used when defining the information describing the suitability of the said nutrient and/or medical substance for the user to such an order that the nutrient and/or medical substance with the highest probability to have a healing effect on the said health property is placed as the most important.

In addition, information related to the user can comprise information describing the user's likings and dislikings, and information describing the user's hobbies and energy consumption both at work and in free time. The information describing a liking can comprise information, for example, about the user's taste and/or smell likings, in which case some scent or flavouring meaningful for the user can be added to the dose of nutrition. A dose of nutrition and/or medication optimal for the user can be planned with the help of the information system. The dose can be, for example, a tablet, capsule, pressed piece, powder, grease mixture, oil, piece of ice, or food, medicament or drink mixture, taking into account the information of the reference group and the user, among others. The reference group can be, for example, sportsmen, such as swimmers, short and long distance runners, shooters or golfers.

Information related to reference groups can comprise, among others, information about what kind of eating habits certain reference groups have, what kind of nutrients and/or medical substances and/or harmful substances they typically get in the nutrition consumed, in what kind of environmental conditions they live and/or work, what is their genetic background, and what illnesses are common in the said reference group. Such reference groups can be, for example, tribes, races and nationalities, such as PIMA Indians, Japanese, Eskimos, Finns, persons in eastern Finland, East/West Germans, Slavs and Australians. Alternatively, the reference group can also be a reference group representing a certain profession group, such as office employee, fireman, forest worker or diver, or sportsmen engaging in certain sports.

The said information can be delivered to the information system, for example, with the help of the program "Fooz-Puzzle-Communicator" (FPC program). The FPC program makes it possible to deliver information directly to the information system in an advantageous pre-processed format, which the database arrangement understands. The user interface of the FPC program can be designed especially according to the needs of a single user, producer of nutrients and/or medical substances, nutrition dispenser and quality control organs, merchant, restaurant personnel or medical personnel.

The FPC program can be run, for example, on a general server, in which case the FPC program can be used via a data network, such as the Internet or digital television, or with the help of a mobile station. The user interface of the FPC program can advantageously be, for example, a form according to the XML and/or XML derivative languages to be offered in the Internet. Information can be delivered to the information system also in some other document format, in which case it can be changed to the XML format and/or the format of XML derivative languages for further processing.

Information related to the user can be gathered from the user himself or the medical authorities treating the user. The user can deliver information about himself, for example, likings and dislikings concerning foods, and information about illnesses, energy consumption, working environment, hobbies and family relations, to the information system. However, the information supplied by the user can be any information reported by the user, which the user can deliver either in numerical form, with the help of a certain code or form, such as a paper form or an electronic form, or alternatively, with the help of free-format text. An electrical form is preferably according to XML and/or XML derivative languages, for example, a form available in the Internet.

The user can deliver his information to the information system, for example, via the Internet, e-mail, digital television or mobile station, by letter or fax or, according to one embodiment, also by phone. Most preferably, the user can deliver the information about the user to the information system with the help of the FPC program.

Information related to the user's nutrition habits can be obtained at least partly from the systems of shops and restaurants selling foods, foodstuffs and/or medical substances and doses to the user, the systems being able to identify the user and register the nutrition information of the food or dose bought and/or consumed by the user, and further deliver the information to the information system of the invention together with the user's identification data.

According to one embodiment, the nutrition dispenser can be provided with a user interface utilising short-range radio technology, such as the Bluetooth technology, and/or a user interface using smart cards/magnetic cards, in which case at least the user's basic information can be stored to the said equipment, such as a mobile station or, alternatively, to a smart card and/or magnetic card. Information related to the user can be delivered to the nutrition dispenser of the invention also, for example, from a server along data transmission networks known for one skilled in the art or, alternatively, at least partly in a data recording device carried by the user, for example, the memory of a mobile station or some other memory equipment, such as on CD disc.

Besides the user's basic information (e.g. name, age, gender), also other information related to the user can be stored to the data recording device, such as the user's length, weight, information describing allergies, likings, special diets, or information about the user's genetic background and structure, genotype (DNA), functional state of genes, tribe, group, nationality, illnesses, mental state, medication, living environment, working environment, type of work, family relations, individual history, work or sports performance, fat percentage, blood pressure, hemoglobin, cholesterol, disease of the locomotor system, depression, cardiac disease, hypertension, asthma, headache, migraine, illness of the psyche, illnesses caused by alcohol, dementia, hormone-dependent cancer, and other essential information to be personified for the user and essential for the dose of nutrition to be prepared, and also at least part of the user's genetic map.

The nutrition dispenser can also be arranged to be compatible with fitness equipment so that as the user is performing a physical exercise, the hardness, duration, effect and energy consumption of the performance, for example, are recorded to a data recording device, from which the information can later be read with the help of the nutrition dispenser of the invention. Such a data recording device can be, for example, a magnetic card, smart card, barcode or a mobile station provided with a method utilising short-range radio technology, such as the Bluetooth technology, in which case the nutrition dispenser preferably includes means for reading the said data recording device, for example, a magnetic card, smart card or barcode reader or a data reader provided with a method utilising short-range radio technology. During the performance or immediately after it, it is also possible to measure other information of the user that can be measured and that are known for one skilled in the art, such as pulse, respiration rate, temperature, blood pressure, muscular electricity graphs, fat percentage, muscular mass, water mass, lactic acid concentration, ability to take oxygen, and $VO_2$ maximum.

The user's information can also be measured with any other device measuring the user's functions and performance known for one skilled in the art, for example, a wrist computer, the information of which can be fed to the nutrition dispenser of the invention during or after the performance. According to one embodiment, the equipment measuring the user's information can also be at least partly integrated to the fitness device used by the user. Data transmission between the equipment measuring the user's information and the nutrition dispenser of the invention can be performed with the help of data transmission methods known for one skilled in the art, for example, by radio or cable.

According to one embodiment, the nutrition dispenser can also be provided with printing equipment, such as a printer or display, in which case the nutrients and/or medical substances personified for the user, their amounts and proportions can be printed to be seen by the user. Nutrition information can also be printed, for example, on paper or to the side of a serving dish of the dose, such as a bottle. In this case, the user can feed the information about the substances contained in the dose, for example, to the database arrangement of the information system by delivering the information via an information network, such as mobile station, SMS (Short Message Service), e-mail, the Internet, or digital television or, alternatively, via traditional mail.

According to an advantageous embodiment, the nutrition dispenser of the invention can deliver the information about the nutrients in the doses of nutrition prepared by it via a short-range radio link, such as the Bluetooth technology, to the user's mobile station, to the user's smart card with the help of the smart card read/write equipment, or to the user's magnetic card with the help of the magnetic card read/write equipment, in which case the user can deliver the information further to the database of the information system, for example, from his own computer. The user's computer can be provided with a reading device utilising short-range radio technology, such as the Bluetooth technology, and/or smart/magnetic card reading device or barcode reader, and with equipment for communicating with the information system.

According to an embodiment of the invention, the nutrition dispenser of the invention can also be arranged to be in data transmission connection with the information system so that the nutrition dispenser can find out about the user's genetic background, allergies, nutrients consumed by the user, likings, and about other above defined matters essential for the dose of nutrition and/or medication to be personified and prepared for the user. Alternatively, the information system can at least partly define the nutrients and/or medical substances suitable for the user, their amounts and proportions by utilising at least partly the database arrangement of the information system, and possibly, information related to the user and his environmental conditions, such as sports performance, and deliver the information about the nutrients and/or medical substances to be used for the dose, their amounts and proportions to the nutrition dispenser for preparing the dose of nutrition and/or medication to be personified for the user. According to an embodiment of the invention, the nutrition dispenser can also comprise at least part of the information system, its information unit and database arrangement, and thus it can also itself define the information of the nutrients and/or medical substances to be used in the dose, such as amounts and proportions, and to deliver it then directly to the user's database in the information system with the help of telecommunications equipment.

Defining the nutrients and/or medical substances suitable for the user can be realised at least partly by analysing the amount and quality of nutrients previously consumed by the user and other information needed in the forming of an individualised optimal dose of nutrition. The information on nutrients previously consumed can comprise information, for example, from one or several days, such as a week or a month. Information about the nutrients and/or medical substances consumed by the user can be in unprocessed or pre-processed form, for example, in the database arrangement, to the information of which the information system of the nutrition dispenser of the invention has access.

For defining the optimal dose of nutrition and/or medication for the user, among others, the user's state of health can be analysed, for example, from the database arrangement comprising the user's health information, the information system used by the nutrition dispenser of the invention having access to the information. In addition, the user's genotype, i.e. the user's genetic information or at least part of the user's genetic map can be observed; the genetic map can be stored, for example, to a genetic map database of the database arrangement, to the information of which the information system used by the nutrition dispenser of the invention has access, or it can be at least partly stored to a data terminal equipment used by the user, such as a mobile station. Further, scientific research information can be observed at least for the parts which are necessary. Scientific research information can be stored, for example, to some database arrangements, to the information of which the information system used by the nutrition dispenser of the invention has access.

With the help of the nutrition dispenser of the invention, also the user's gender can be taken into account when planning an optimal dose. For example, for women in menopause, the dose of nutrition can be made to include certain isoflavonoids, such as phormononetines of clover, for example biocanine A or cumestan, or lignans, which are plant estrogens and which influence the hormone metabolism in many ways and, for example, in ways preventing cancer.

The dose of nutrition and/or medication defined and prepared by the nutrition dispenser of the invention can preferably include both sugar that fast increases the blood sugar level, such as glucose, and sugars with a long-term effect, such as fructose, and additionally caffeine and guarana and at least one flavonoid. As is well known, caffeine has a fast stimulating effect. To balance this effect, guarana extract can be advantageously used in the dose prepared by the nutrition dispenser, which is an agent with a slower stimulating effect than caffeine, but which also increases concentration. Because of this, the caffeine content of the dose of nutrition can be kept relatively low, which for its part reduces the manifestation of the harmful effects of caffeine, such as muscular tremor or increase in blood pressure, with people sensitive to caffeine. Nevertheless, an effective stimulating effect is achieved by the joint effect. Also taurine can be used in connection of other stimulating agents because of its stimulating properties.

Advantageous embodiments of the invention are next explained in more detail, referring to the enclosed drawings, in which FIG. 1 is a block diagram of an exemplary nutrition dispenser according to the present invention;

Figure 6:
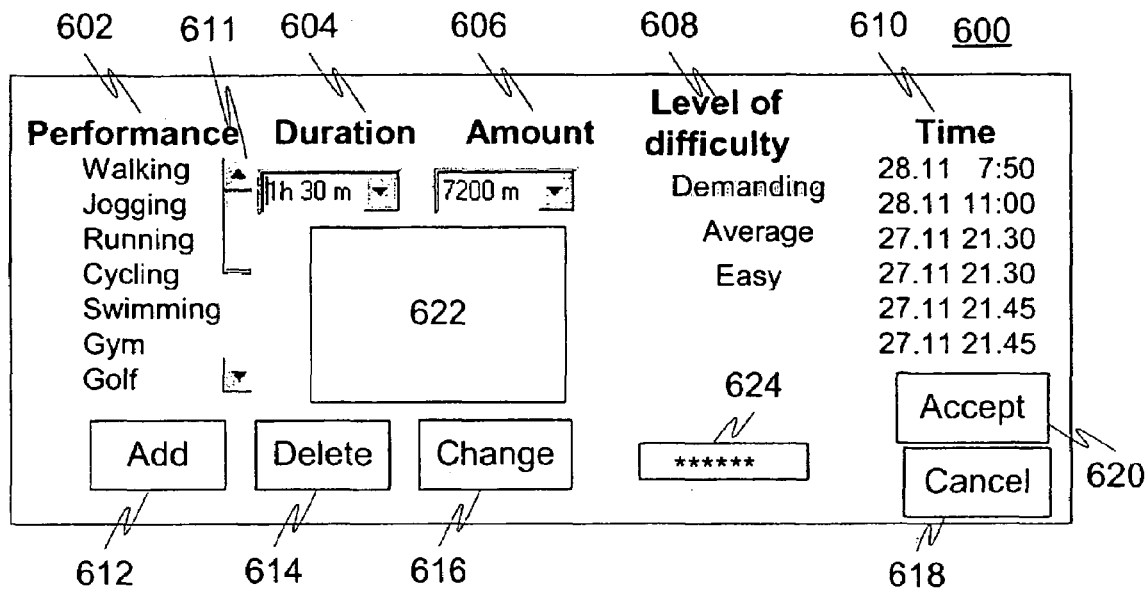
Figure 7:
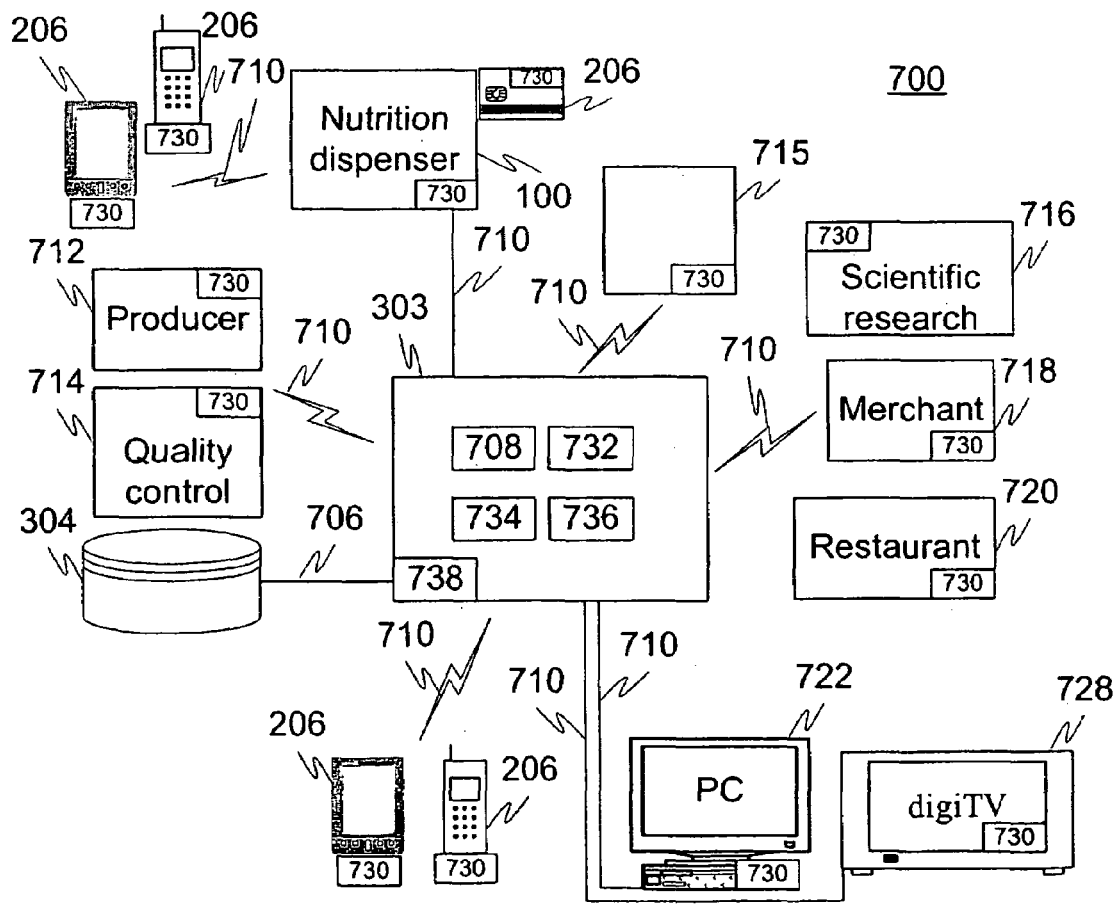
Figure 8:
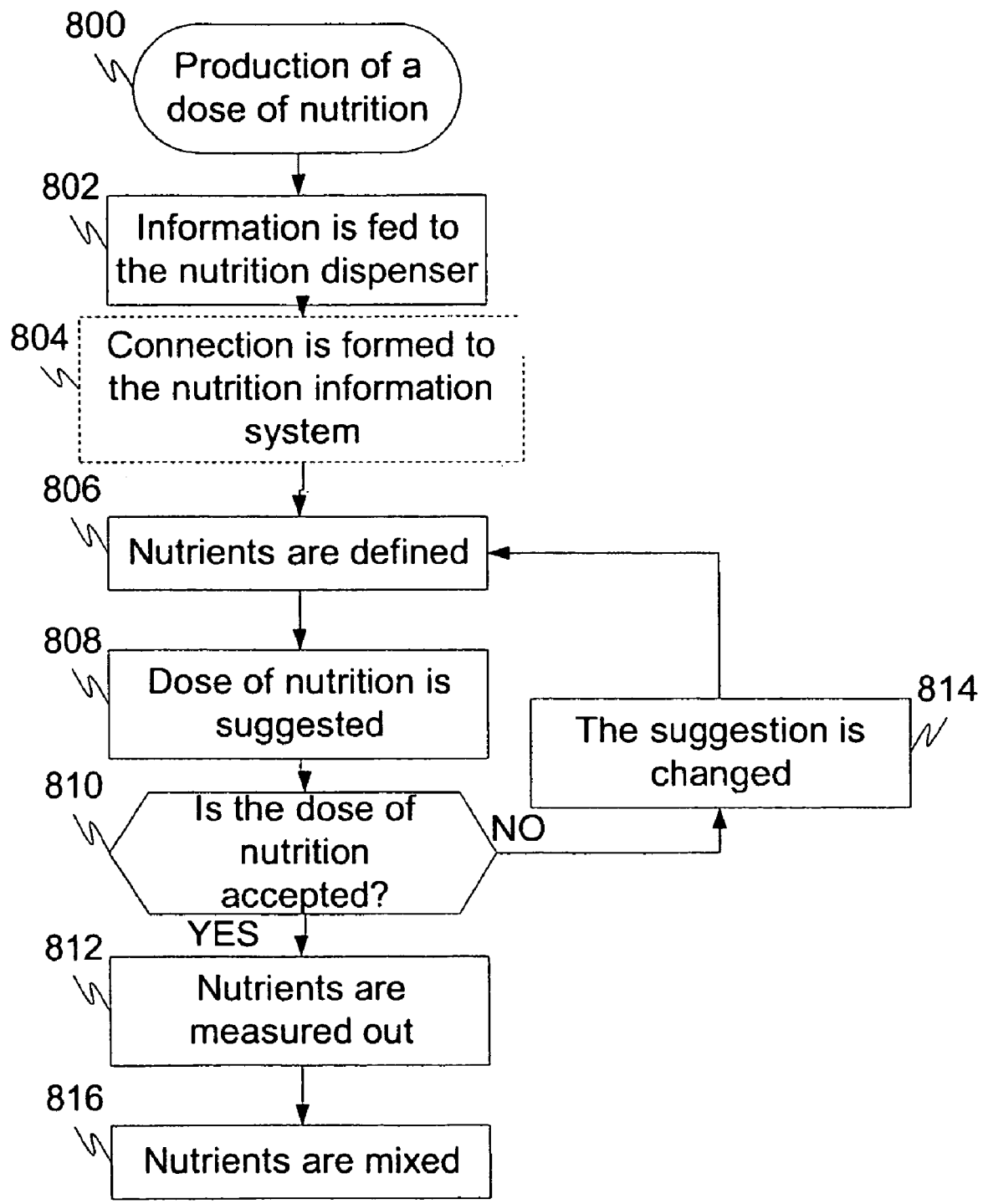

FIG. 6 presents an exemplary user interface of the FPC program for gathering information describing the user's energy consumption and environmental conditions according to the present invention;

FIG. 7 is a block diagram of an exemplary system for gathering nutrition information and for forming individualised nutrition information according to the present invention; and FIG. 8 is a flowchart of a method for producing nutrition suitable for the user with the help of the nutrition dispenser according to the present invention.

Figure 1:
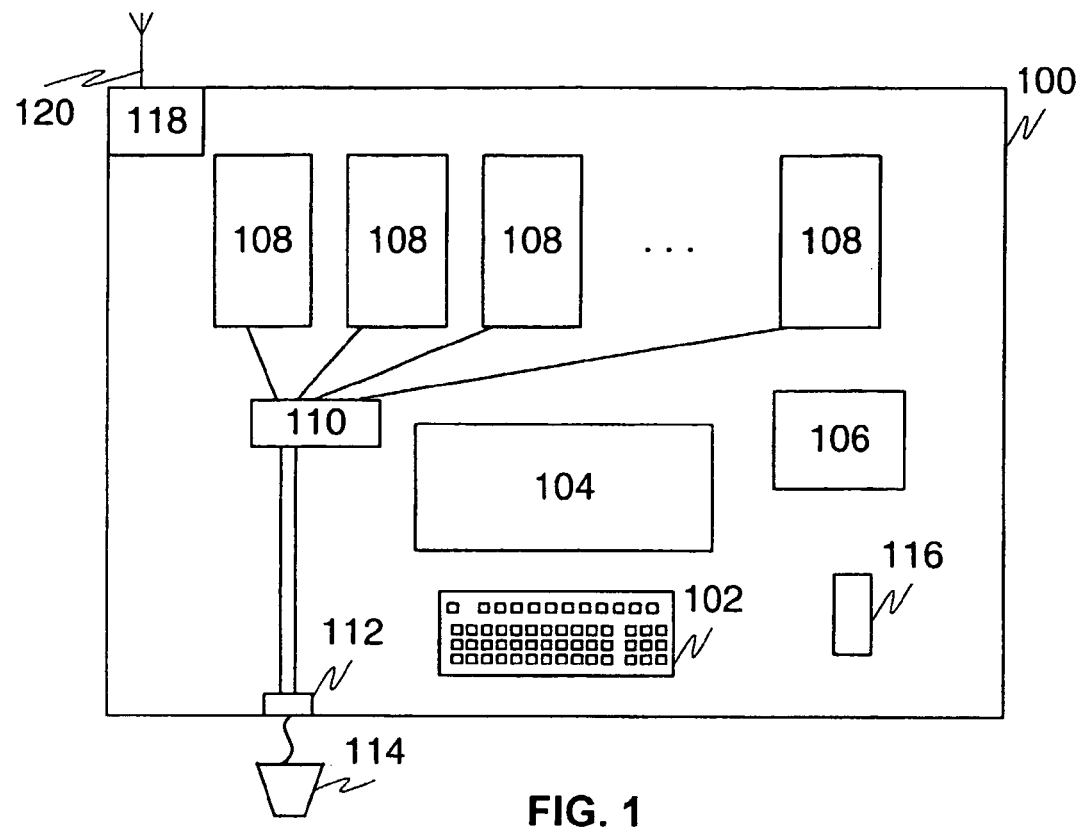

FIG. 1 is a block diagram of a nutrition dispenser 100 for defining and preparing a dose of nutrition and/or medication to be personified for the user in accordance with the present invention. The nutrition dispenser 100 of the invention comprises, even at its simplest, the user interface 102, with the help of which the user can feed information to the nutrition dispenser. The user interface 102 can be, for example, a keyboard or a control stick or some other information supply device known for one skilled in the art. The user can feed information, for example, about his age, gender, possible nutrient and/or medical substance limitations, such as allergies, and information about environmental conditions, such as temperature, energy consumption, type, level of difficulty and duration of a sports performance. In addition, the nutrition dispenser can have the display 104, such as a liquid crystal display or picture tube display, for presenting the information to the user. For example, questions to the user and information fed by the user can be presented on the display. In addition, a suggestion for the dose of nutrition and/or medication to be prepared for the user can be presented on the display, and also information about substances in the dose, in which case the user can either accept or reject the suggestion.

The nutrition dispenser 100 of the invention can also comprise the equipment 106 for defining the nutrients and/or medical substances suitable for the user, their amounts and proportions with the help of information fed by the user and the database arrangements used by the nutrition dispenser 100. The equipment 106 can most preferably be realised with the help of an information system utilising fuzzy logic and an information unit, and with the help of the software used by them and the database arrangement 500 (FIG. 5), which comprises information related to the relation between at least one piece of information to be asked from the user, such as age, gender, length, weight and energy consumption, and some nutrient and/or medical substance.

In addition, the nutrition dispenser 100 comprises rooms, such as containers 108 for storing different nutrients and/or medical substances. The containers can be cooled, air-tight, moisture-proof and/or heated, depending on the substance to be preserved. The substances are most preferably arranged each to an own container 108, in which case, when preparing a dose personified for the user, the required substances can be measured out in appropriate amounts from the different containers 108 with the help of a special dosing device 110. From the dosing device 110, the nutrients and/or medical substances are forwarded to the mixer 112, with the help of which the substances are mixed to a finished dose of nutrition and/or medication and into a form to be consumed by the user. The dose can most preferably be mixed to the bottle 114.

In addition, the nutrition dispenser 100 can comprise the equipment 116 for collecting a charge from the user. The charge collection equipment 116 can be any charge collection device known for one skilled in the art, such as a coin/note automate, bank card reader, or a call number liable to charge. The nutrition dispenser 100, especially the nutrition dispenser 100, which is not connected to a data transmission network, can further be provided with the equipment 118 and 120 for updating the software (e.g. in the equipment 116) used by the nutrition dispenser 100, for example, via the mobile station network. Updating the software can also be performed with other methods, such as CD discs or other similar equipment.

Figure 2:
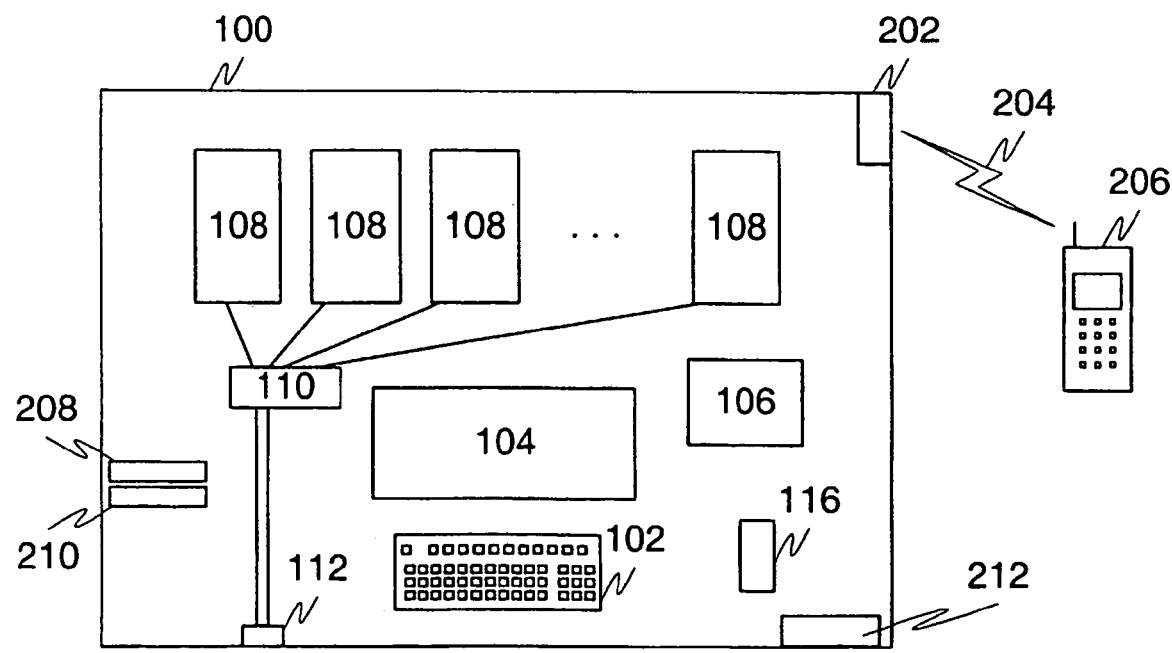
FIG. 2 is a block diagram of an exemplary system for arranging the nutrition dispenser according to the present invention.

FIG. 2 is a block diagram of a system for realising the nutrition dispenser 100 in accordance with the present invention. Again, the nutrition dispenser 100 can comprise the user interface 102, the display 104, the equipment 106, the containers 108, the dosing device 110, the mixer 112, the possible serving dish 114, and possibly also the charge collection equipment 116.

According to one embodiment, the nutrition dispenser 100 can further be provided with the user interface 202 utilising short-range radio link, such as the Bluetooth technology, and with the telecommunications connection 204, with the help of which the user's information can be fed to the nutrition dispenser 100. For example, the user can have his basic information stored to some portable data processing device 206 utilising short-range radio link, such as his mobile station, in which case the nutrition dispenser 100 of the invention can identify the user's information and the information essential for the dose of nutrition and/or medication to be prepared for him without the user having to separately feed them. According to one embodiment, the user can be shown the information read about the user on the display 104 of the nutrition dispenser 100, in which case the user can still change it before the dose is defined and prepared.

It especially has to be noted that the data transmission connection 204 can be a full duplex connection, in which case after defining and accepting the dose the nutrition dispenser 100 can write the information about the nutrients and/or medical substances in the dose personified for the user to the memory of the user's data processing device 206, such as a mobile station. In this case, the user can feed information about the nutrients and/or medical substances later, for example, to the information system, containing his information. In addition, it has to be noted that, according to one embodiment of the present invention, the user interface comparable with the user interface 202 can also be realised with the smart card read/write equipment 208 or magnetic card read/write equipment 210. The nutrition dispenser 100 can also be provided with the printing equipment 212 so that the nutrients in the dose of nutrition personified for the user, their amounts and proportions can be printed to the user.

Figure 3:
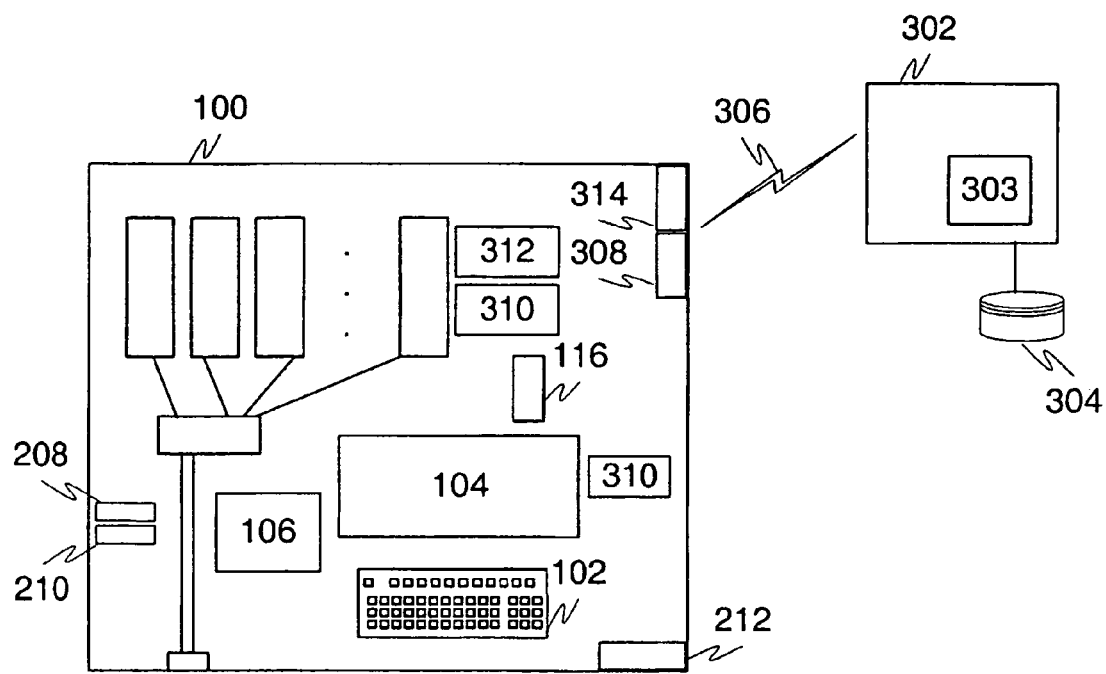
FIG. 3 is a block diagram of an exemplary system for arranging the nutrition dispenser according to the present invention.

FIG. 3 is a block diagram of a second system for realising the nutrition dispenser 100 according to the present invention. The nutrition dispenser 100 can again comprise the user interface 102, the display 104, the equipment 106, the containers 108, the dosing device 110, the mixer 112, the possible serving dish 114, and possibly also the charge collection equipment 116. In addition, the nutrition dispenser can also comprise at least part of the equipment 202, 208 and 210.

According to one embodiment of the invention, the nutrition dispenser 100 can also be arranged to be in telecommunications connection 306 with the information system 302 and its nutrition information unit 303, in which case the nutrition dispenser 100 can, for example, observe the information from medical and biological research results, about the user's genetic background, nutrients consumed by the user, likings and other matters significant for the dose of nutrition and/or medication to be personified and prepared for the user from the databases and database arrangements 402 of the information system 302. In addition, the nutrition dispenser 100 can deliver to the user the information about the personified dose of nutrition and/or medication defined and prepared by it to the database arrangement 304 concerning the user of the information system 302.

For realising the telecommunications connection 306, the nutrition dispenser 100 can be provided with appropriate equipment 308 known for one skilled in the art, such as a modem or network card and appropriate software. The nutrition dispenser 100 can also comprise the equipment 310 for identifying the user with the help of the user ID and password. According to one embodiment, the nutrition dispenser 100 can have access to the user's information in the nutrition information system 302, as the user has fed his user ID and password correctly or as the user has otherwise been identified. Also after this, the nutrition dispenser 100 can write the information about the dose of nutrition and/or medication personified for the user to the nutrition information system 302 and to the database 304 comprising the user's information.

In addition, the nutrition dispenser 100 can deliver information fed by the user to the information system 302 via the telecommunications connection 306, in which case the information system 302 can at least partly define the nutrients suitable for the user, their amounts and proportions by utilising at least partly the databases 304 of the information system 302 and the equipment using fuzzy logic, such as the information unit 303, and information possibly delivered by the nutrition dispenser 100 related to the user and environmental conditions, such as a sports performance. The information system 302 can also deliver information to the nutrition dispenser 100 via the telecommunications connection 306 about the nutrients and/or medical substances to be used for the dose of nutrition to be personified for the user, their amounts and proportions for preparing the dose to be personified for the user. The nutrition dispenser 100 can also itself define information about the nutrients to be used for the dose and to deliver it then directly to the user's database 304 in the information system 302 via the telecommunications equipment 306.

The nutrition dispenser 100 can also have the equipment 312 for utilising the FPC program in the delivery of information between different subjects, such as the nutrition dispenser 100 and the information system 302. In addition, the nutrition dispenser can have the equipment 314 for charging the user via the information system 302.

Figure 5:
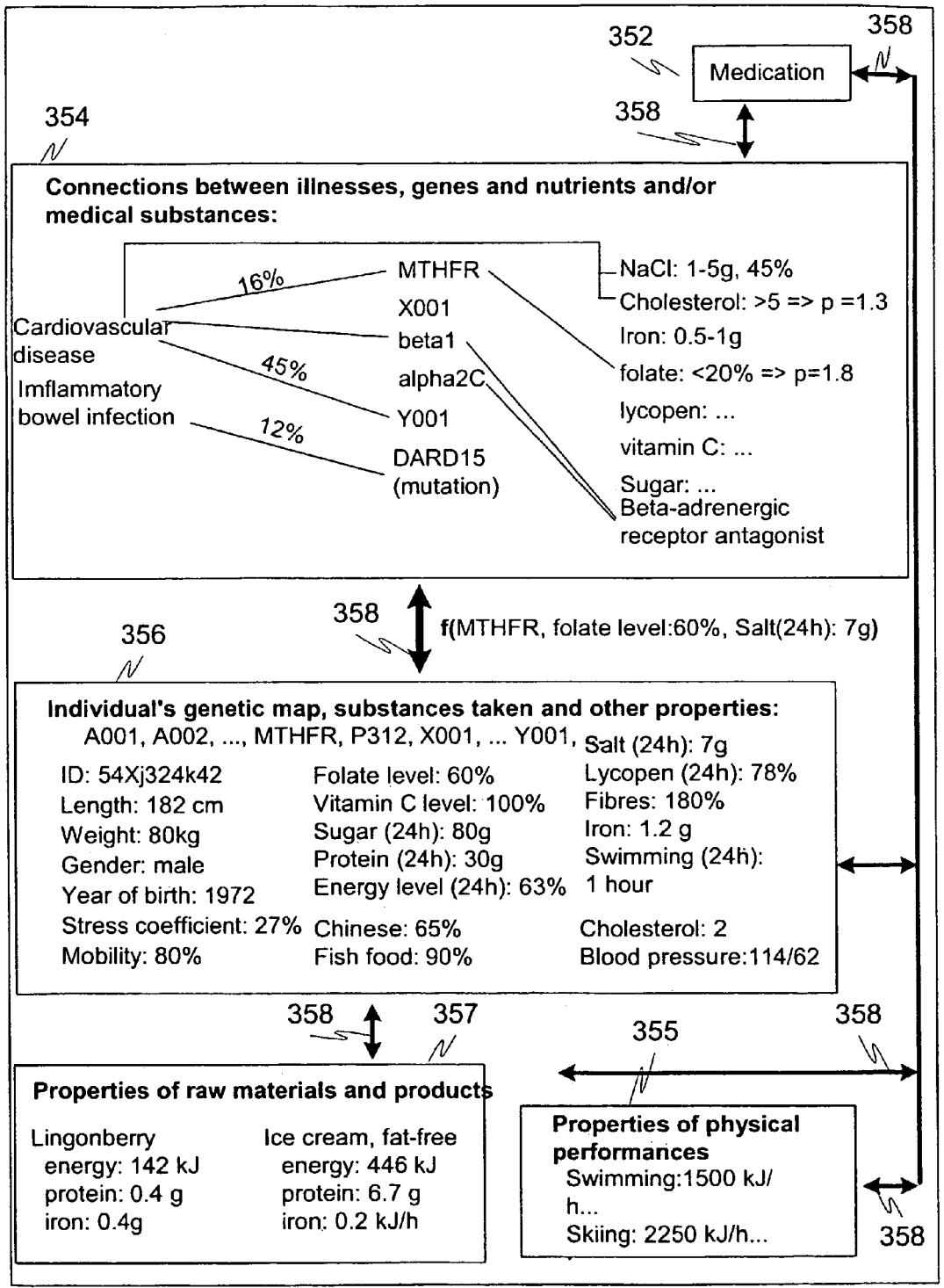
FIG. 5 is a diagram of an exemplary database arrangement for storing and arranging information essential for the invention according to the present invention.

However, it has to be noted that the embodiment in FIG. 3 is exemplary and that the nutrition dispenser 100 can also be arranged so that at least part of the information system 302, its information unit 303 and/or databases or database arrangements 304 comprising, among others, the exemplary database arrangement 500 shown in FIG. 5, is integrated to the nutrition dispenser 100.

Figure 4:
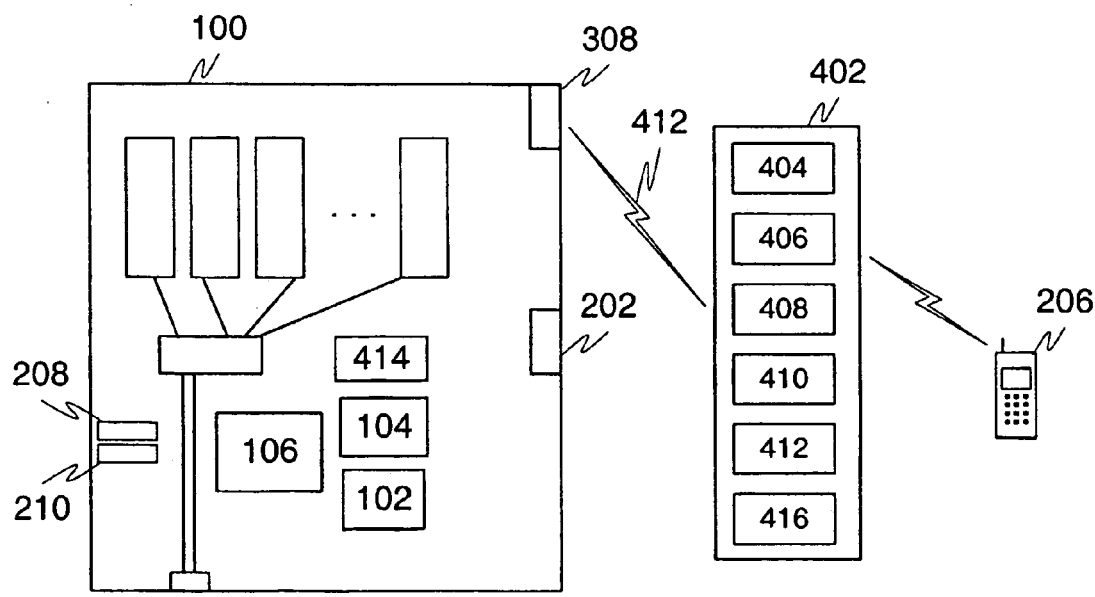
FIG. 4 is a block diagram of a second exemplary system for arranging the nutrition dispenser according to the present invention.

FIG. 4 is a block diagram of a system for realising the nutrition dispenser 100 in accordance with the present invention. The nutrition dispenser 100 can again comprise the user interface 102, the display 104, the equipment 106, the containers 108, the dosing device 110, the mixer 112, the possible serving dish 114, and possibly also the charge collection equipment 116. In addition, the nutrition dispenser can also comprise at least part of the equipment 202, 208 and 210, and of the equipment 308, 310 and 312.

According to one embodiment of the invention, the nutrition dispenser 100 can be arranged to be compatible with fitness devices 402 or similar devices that are, for example, used in gyms so that, as the user is performing some physical exercise, information about the user's performance can be stored to some data recording device, from which the information can afterwards be read with the help of the nutrition dispenser 100 of the invention. The fitness device 402 and/or the user can be provided with the equipment 404 measuring the user's performance, with the help of which some information essential for the sports performance and/or nutrition information known for one skilled in the art can be measured; such as the user's information, pulse, energy consumption, duration and level of difficulty of the sport performance.

The fitness device 402 is preferably arranged to deliver the information measured by it to the user. For this purpose, the fitness device 402 can have, for example, the equipment 406 realised by short-range radio link, such as the Bluetooth technology, with the help of which the information can be delivered to the user's data processing device 206, such as mobile station. Alternatively, the information can also be delivered to the user's magnetic or smart card using the magnetic or smart card read/write equipment 408. According to one embodiment, the fitness device 402 can also comprise the printing equipment 410 for printing the information on paper, for example, as plain text or as barcode, in which case the nutrition dispenser can have the equipment 414 for reading and interpreting the barcode. In addition, the information can be delivered from the fitness device 402 to the nutrition dispenser 100 of the invention also using other data transmission methods known for one skilled in the art, such as the telecommunications connection 412. In this case, the fitness device has to have the appropriate equipment 416 for connecting to the telecommunications connection used and to the nutrition dispenser 100.

FIG. 5 is a diagram of an exemplary database arrangement 500 of the database 304 of the information system 302 for storing and arranging information essential for the invention. The database arrangement 500 can preferably comprise several databases and sub-database arrangements 352, 354, 355, 356 and 357. In addition, the database arrangement can be a distributed database arrangement, in which case at least one first part of the database arrangement can be stored using at least one first recording device and at least one second part of the database arrangement can be stored using at least one second recording device. Information can be transmitted between the database arrangements, for example, by delivering the desired variables as parameters 358; for example, part of the user's genetic map, and information about nutrients and/or medical substances consumed by the user.

Information can be stored to the database arrangement of the invention most preferably in a processed, predefined format. For example, information concerning genes can be fed and stored to the database arrangement on the basis of genetic tests made to an individual preferably in a processed form as facts, with the help of which information about gene forms exposing to illnesses is expressed. Facts concerning genetic tests can be expressed, for example, as character string combinations: "<gene form/–dot>+<result>", in which the result is either positive or negative, or possibly a weighting value, such as a numerical value between –100-+100, describing the weighting value of a gene or its significance in relation to an illness.

Alternatively, facts can be expressed in a form, in which the probability is directly reported, with which the said gene or genotype exposes to a certain illness, such as the fact that persons with the genotype of methylenetetrahydrofolate reductase (MTHFR), which is a genetic change leading to high homocysteine levels, have a 16% higher risk to fall ill with cardiovascular disease than persons, who do not have this genetic change. The database arrangement can have a cross reference from the MTHFR genotype, among others, to the folate level, because there exists a scientific fact that the risk to fall ill with a cardiovascular disease is especially high, if the user's folate level is low, in which case the probability to fall ill with a cardiovascular disease can be increased by a certain weighting coefficient, if the user's folate level is below the intake limit for the folate level. For example, if the folate level is below 20%, the weighting coefficient can be 1.8, with which the probability (here 16%) to fall ill with a cardiovascular disease is weighted so that the probability can rise, for example, to 29% (1.8·16%=29%). Taking the weighting into consideration can also be performed by other mathematical methods besides multiplication.

In addition, the said exemplary database arrangement can also have a cross reference to nutrients and/or medical substances, with which deficiency caused by nutrients can be reduced; for example, the said folate level can be raised, in which case the information system according to the invention can suggest the said nutrient and/or medical substance to the user, for example, for raising the folate level and for reducing the risk to fall ill with a cardiovascular disease. Nowadays it is well known that raising the folate level, for example, with the help of a diet is advantageous with persons with the MTHFR genotype.

The facts can alternatively be presented also in some other appropriate way.

Among others, information about analysis results concerning the contents of the researched raw materials/products generated by the quality control unit can also be stored to the database arrangement. The information can be presented, for example, as pairs of substance—measurement result, which are stored to the database as combinations (pairs) of the character string combination and the real number presenting the measuring result needed for the identification of the product; for example, lingonberry, iron 0.4 g. The database can also include a section, in which it is told what is the unit of measure of the real number presenting each measurement result (e.g. mg/100 g). There can be as many said pairs in the database as there are measurements made.

The information generated by the producer can consist of measurement results of the said type and of information concerning growth conditions and growth. The latter category is presented in the database typically as a combination of the character string needed for the identification of the product, the fields determining the location and other conditions of growth (as character strings), and the field specifying calendar information (defining the date: date-month-year, and when required, the time: hours/minutes). Further, also information about transports is stored to the database in an appropriate way. A certain probability or weighting coefficient between the said information and different illnesses, with which the condition defined by the said piece of information or some other parameter exposes to the said illness or protects from the said illness, can be arranged to the database of the invention.

Also information concerning the user's likings and restrictions can be stored to the database arrangement 500. Information describing likings can be stored to the database, for example, as a set of character strings, each of which specifies a single liking, such as "sun-dried tomato a'la Beato" and "onion", or a category of likings, such as "Chinese". Along with every character string, also information about the direction and extent of the liking can be stored, for example, by coding it as an integral number between −100 . . . +100, in which −100 describes total disliking, 0 neutral, and +100 total liking, respectively. Information concerning foodstuff restrictions can be stored to the database, for example, as a set of character strings, each of which specifies the category of a single foodstuff category, such as "gluten", "milk protein" or "E407" (additive, in this example carrageen).

According to one embodiment of the invention, scientific information describing the relations between different illnesses and foodstuffs and/or forms of genes can be fed and stored to the database arrangement 500 by gathering it from scientific publications, for example, in a form of rules, in which the condition part of the rule (can consist of one or several separate conditions) and the inference part are given. A probability value (for example, between −100 . . . +100 or, alternatively, exposure risk increased by 16%) and, according to one embodiment, also the weighting coefficient, such as p=1.8, can be connected to each rule. The said scientific information typically consists of (1) the effect of nutrition on morbidity (positive and negative effects; protective and exposing effects), (2) the effect of medicaments on morbidity (positive and negative effects; protective and exposing effects), (3) the effects of genes on morbidity (positive and negative effects; protective and exposing effects), (4) combinations of all above-mentioned factors (in the rule part, 0-n conditions from each sector). The rules are typically of the format: IF condition 1 AND condition 2. . . AND condition N SO illness PROBABILITY X, in which X can be a value, for example, between −100 . . . +100. The value −100 can express, for example, that as the conditions are fulfilled, the illness would be avoided with the probability of 100%, and the value +100 can express, for example, that the illness is unavoidable if the said conditions are fulfilled. Alternatively, the values can also be selected from another set of values, and they can be standardised in an arbitrary way according to methods known to one skilled in the art.

The database arrangement of the invention can advantageously be manifold, so that upon forming a summary of the overall effect of certain nutrients and/or medical substances, also other levels of the database arrangement 500 can be gone through, such as the level 352, which comprises information about the effects of medical substances on different illnesses together with certain genes. With the help of the database arrangement of the invention, it is possible to chart the joint effect of several factors, for example, in a situation, in which a nutrient exposes to an illness with a certain probability, but simultaneously some other nutrient or a characteristic of some other level, such as the effect of a medicament, influences the said exposure in a protective way.

It especially has to be noted that the database arrangement can have primary probabilities, such as the primary probability of 16% that the MTHFR genotype causes cardiovascular disease or that genes X and Y together cause the illness Z1 with a probability of 20%. In addition, the database arrangement can have secondary probabilities or weighting coefficients; for example, an overdose of NaCl increases the risk to fall ill with cardiovascular disease 1.8-fold, if the person has the MTHFR genotype. The primary probabilities are typically related to genes, when again secondary probabilities or weighting coefficients are related to nutrients and/or medical substances, environmental factors and likings, and they can be changed.

The management and processing of comprehensive information sets in the database arrangement 500 of the invention can be realised, for example, with the help of the Websom method utilising self-organising maps (SOM). The user's information can be at least partly in a processed form, stored to the memory equipment of the system, in which case the said part need not be processed again, unless there have occurred changes in the said information after the previous processing.

Also nutrition and/or medical information can be delivered with the help of the database arrangement of the invention in a way, in which the building of nutrient recommendations from prepared nutrient alternatives is made possible, on the one hand, and in which restriction conditions, on the other hand, are taken into account, the restriction conditions consisting of basic information, such as nutrient contents, genetic information and personal information, and of the principles in rule form describing the healthfulness of these combinations presenting scientific information.

After this nutrition information, such as defining the compositions of the doses of nutrition and/or medical substances to the nutrition dispenser, can be produced in a way, in which the building of nutrient recommendations from completed nutrient alternatives is made possible, on the one hand, and in which restriction conditions, on the other hand, are taken into account, the restriction conditions consisting of basic information, such as nutrient contents, genetic information and personal information, and of the principles in rule form describing the healthfulness of these combinations presenting scientific information.

According to one embodiment of the invention, two different operation models can be presented to the user, such as a model, in which the individual chooses the virtual dose of nutrition and/or medical substance he wants from the options offered in the nutrition dispenser, which options can be presented to the user graphically, for example, with the help of display of the nutrition dispenser. After the user has selected his virtual dose, the information system 302 can check the suitability of the option for the user, for example, with the help of the database arrangement 500 and point the deviations and/or direct to better options. Alternatively, a prepared dose can be formed to be suggested to the user, which can be compiled of single doses of nutrition and/or medication, taking into consideration the information in the database arrangement 500.

Forming the said dose to be suggested to the user can be performed, for example, as a series of measures, in which a dose option is first asked from the individual, and contents information concerning the dose is gathered from the database arrangement 500. After this, the contents information of the dose option can be compared with each information category in the database arrangement 500. If there are found inconsistencies, for example, if the cumulative amount of a certain nutrient and/or medical substance is higher or lower within a certain period of time, the inconsistency information can be stored to the read-alter storage, for example, by storing the intensity/significance of the inconsistency. After all contents information has been gone through, the most intensive/important inconsistencies and their effects on the user's health and/or metabolic state can be found out, and some substance can either be suggested to be added or reduced on the basis of the cumulative amount and intake limit of the substance, or a replacing nutrient or contents element can be endeavoured to be found from the database arrangement to replace the nutrient and/or contents element causing the inconsistency so that the probability with which the said nutrient and/or medical substance exposes to some illness would be as low as possible or that the probability with which the said nutrient and/or medical substance protects from some illness would be as high as possible.

When as suitable a dose as possible has been formed to the user, the dose can be presented to the user, for example, with the help of a graphic food plate, the graphic food plate presenting the suitable nutrients and/or medical substances, for example, with the help of a sector, which is proportioned to the amount of the nutrient and/or medical substance. Alternatively, the dose can be presented also as a text version in plain text, depending on the situation of use.

In the database arrangement 500, the information can be presented, for example, in rule form (so-called Horn clauses supplemented by probability values, cf. R. Kowalski, Predicate logic as a programming language. In Proceedings of IFIP 74, pages 569-574, Amsterdam, 1974. North Holland). The inference mechanism needed to form the suitable dose of nutrition and/or medication or food plate can be realised, for example, by using the Horn clauses supplemented by probability values. For example, assumption-based inference can be used in the realisation of the inference mechanism (e.g. J. de Kleer. An assumption-based TMS, Journal of Artificial Intelligence. 28. 127-162. 186), likewise the mathematical reasons that are the foundation for this (e.g. A. Dempster. Upper and lower probabilities induced by multi-valued mapping. Anneals of Mathematical Statistics. 38. 325-339. 1967. G. Shafer. The Mathematical Theory of Evidence. Princeton University Press. 1976). Alternatively, the inference mechanism can also be realised in some other appropriate way.

It especially has to be noted that the database arrangement can contain considerably more references than in the example of FIG. 5. For example, one gene can influence several different illnesses, likewise also a nutrient and/or medical substance. In addition, different genes together can generate a different joint effect than all genes taken into account individually. Further, there can be considerably different numerical directives and references between physical performances and energy consumption, such as one hour of swimming corresponds to 1,500 kJ of energy.

FIG. 6 presents an exemplary user interface 600 of the FPC program for gathering information about the user's energy consumption and environmental conditions in accordance with the present invention. The user interface 600 can be presented and run, for example, with the help of the display and controllers of the nutrition dispenser of the invention, such as a touch screen or keyboard. The user interface 600 can be realised, for example, with the help of the XML or an XML derivative language so that the information fed to the user interface can be delivered to the information system 302 via a data transmission connection.

The user interface 600 typically comprises the field 602 for defining the physical performance performed by the user, such as walking, jogging, gym and swimming, the field 604 for defining the duration of the physical performance performed, such as 1 hour and 30 minutes, and the field 606 for defining the quantity of the physical performance performed, such as 7,200 metres. The user interface 600 can also comprise the field 608 for defining the level of difficulty of the physical performance defined, such as, for example, demanding, average or easy, and the field 610 for defining the time when the physical performance was performed.

The field 602 for defining physical performance can also comprise a sub-menu, in which case the user can define the type of the performance in a more exact way. By using the sub-menu, the user can select from the sub-menu, for example, that the running defined in the field 602 is terrain running. Likewise, also the other fields 604, 606, 608, 610 of the user interface 600 can comprise at least one specifying sub-menu.

Alternatively, at least part of the fields 602-610 of the user interface 600 can be realised in some other way besides menu fields. The fields 602-610 can also be fields, to which text can be written in free form; for example, "Terrain running, 7,200 m". Also a code defining the desired value for the parameter defined by the said field can be written to the fields. The code equivalent to terrain running can be, for example, Jm, in which case the user can directly write the code "Jm" representing terrain running to the performance field 602. The code can typically comprise letters, numbers and/or special characters.

According to one embodiment, the user can have a barcode table describing the different parameters of the fields 602-610 and a barcode reader, in which case the user can, for example, activate each field 602-610 in turn from the user interface and read the information about the performance, duration, amount, level of difficulty, and time from the barcode table using the barcode reader, such as a barcode pen. The user interface 600 of the FPC program can also have selection controllers, for example, scroll bars 611, for selecting the parameters.

In addition, the user interface 600 can comprise keys for performing the commands; for example, the "Add" key 612, the "Delete" key 614, the "Change" key 616, the "Cancel" key 618, and the "Accept" key 620. The "Add" key 612 can be used for adding, for example, several performances to the field 602. The "Delete" key 614 can be used for deleting parameters already defined from the fields 602-610, and the "Change" key 616 can be used for changing the parameters in the fields 602-610. Further, the "Accept" key 620 can be used for accepting and sending the filled-in user interface form 600 to the information system. Alternatively, the "Cancel" key 618 can be used for interrupting the operation.

The user interface 600 according to the invention can further comprise the field 622 for writing free-form text to the data server. The user interface can also include the field 624 for writing the user's user ID and/or password so that one can make sure that outsiders cannot change and/or read the information of other users.

According to one embodiment of the invention, the user interface 600 of the FPC program is a learning user interface, in which case an own profile can be advantageously made for each user to the user interface. In this case, the user interface can learn the physical sports habits of each user, for example, according to the times of day so that the user interface is able to anticipate situations and suggest to the user certain physical performances often performed by the user, their durations, amounts, levels of difficulty and/or times of performance. For example, the user interface can suggest to the user, who walks 1.6 km each weekday morning, and swims 1000 m every Tuesday and Thursday evening, the said performances as default value. In this case, the user only has to accept the suggestion.

Alternatively, the user interface 600 can be at least partly presented graphically so that the user can add information describing his performances by using a controller, such as a mouse, keyboard or touch screen; for example, by pressing, pointing or hauling icons and/or pictures describing the performances, their levels of difficulty and duration. According to one advantageous embodiment, information about the user's sports performance can be transferred to the nutrition dispenser and further to the FPC program automatically, if the information related to the user's performance has been stored to some data transmission equipment, such as on paper as a barcode, to a smart card/magnetic card, or the equipment using the Bluetooth technology, for example, by the fitness device used by the user, and if the nutrition dispenser has been provided with equipment supporting the said data transfer equipment, such as a card reading device. In this case, information related to the user's performance can be presented on the display of the nutrition dispenser, for example, with the help of the user interface of the FPC program, in which case the user can still change the information, e.g. in a way presented above.

However, it has to be noted that the user interface 600 according to the invention for gathering information describing the user's energy consumption and environmental conditions can also comprise a considerably higher number of different fields for the more exact identification of the information about energy consumption or environmental conditions and a considerably higher number of different keys or selection controllers for performing different functions. Alternatively, the user interface 600 of the invention can be realised by using a smaller number of fields, keys and selection controllers than in the embodiment of the user interface shown in FIG. 6. It still has to be noted that, in addition to the said fields, the user interface 600 can have a field, to which the optimal nutrition information and instructions for reaching the optimal nutritive and/or metabolic state generated by the information service of the invention are returned as default value.

Further, it has to be noted that, according to one embodiment of the invention, the information system can also form suggestions for physical performances and to present the optimal physical performance formed by it and the level of difficulty and duration of the performance with the help of a user interface similar to the user interface shown in FIG. 600. The suggestion can also be delivered graphically, at least in part.

In addition, the user interface can also have other fields and/or menus for gathering other information, such as information about the user and the user's dose of nutrition.

FIG. 7 is a block diagram of an exemplary system 700 for updating the information to different systems and for forming optimal nutritive and/or medical information. The system 700 typically comprises the information unit 303 of the information system for forming individualised and optimal nutritive and/or medical information in order to gather the required information of different types and for forming individualised nutritive and/or medical information. Most preferably the information unit 303 can be, for example, a server in the information network, comprising the equipment needed for the formation of individualised nutritive and/or medical information, to which the nutrition dispenser 100 can be connected, for example, via the telecommunications connection 710 known for one skilled in the art. The information unit 303 can alternatively produce information also to other equipment, such as the transmission network of digital television or through the Internet to the user's home computer.

The information unit 303 typically comprises the database equipment 304 for storing the information. The database equipment 304 can comprise, for example, a database arrangement similar to the database arrangement 500 shown in FIG. 5. The information can be, for example, information concerning foodstuffs, genetics, biological, medical, analysed biological and medical research, and information describing the user and the user's situation-specified information, and information describing the user's environment. In addition, the database equipment 304 can contain information referring to reference groups, such as information related to certain tribes or nationalities, and information related to their possible illnesses, living environment and foodstuffs typically consumed by them. The database equipment 304 can be integrated to the information unit 303 of the information system at least in part or, alternatively, the database equipment 304 can be distributed separately from the information unit 303 so that the information unit 303 has the data transmission connection 706 to the database equipment 304.

The information unit 303 typically comprises also the equipment 708 for generating the data transmission connection 706 and 710 with the other parties, such as the nutrition dispenser 100, the producer 712, the quality control unit 714, the medical personnel unit 715, the scientific research unit 716, the shop system 718, and the restaurant system 720. In addition, the information unit 303 can be arranged to be in data transmission connection 710 with the user via a data terminal equipment, such as the computer 722, the mobile station 724, the PDA device 206 and/or the digital television 728.

The information unit 303 can also comprise the equipment 736 for identifying each party, such as the nutrition dispenser 100, the producer 712, the quality control unit 714, the medical personnel unit 715, the scientific research unit 716, the shop system 718, and the restaurant system 720 so that each party 100, 206, 712-720 can deliver information about different nutrients, food products and their nutrition contents, or substances contained in them, and about possible illnesses caused by certain foodstuffs and their interrelations, and information about the contents of doses of nutrition delivered to the user.

Information about a dose of nutrition and/or medication bought, ordered and/or consumed by the user can be delivered, for example, from the system of the nutrition dispenser 100, the shop system 718 and/or the restaurant system 720 to the information unit 303 of the information system automatically in connection of the purchase or order. The identification information of the user, needed by the information system, can be stored, for example, to the magnetic card 206 or similar, in which case the user's magnetic card can be read in connection of the purchase or order, and in which case the information of the food products of nutrients and/or medical substances in the purchase or order are relayed to the information unit 303. Alternatively, the user's individualised user ID can be fed into the system of the nutrition dispenser, shop or restaurant, in which case the information of the bought or ordered food product or dose of nutrition is relayed to the information unit 303 of the information system.

The parties 100, 712-728 in data transmission connection 710 to the information unit 303 can advantageously comprise the equipment 730 for performing the FPC program according to the information, for sending and updating the information of the FPC program and for receiving the information to a data terminal equipment 100, 206, 712-728 from the information unit 303. According to one embodiment of the invention, the equipment 730 can also comprise at least partly the information unit 303 of the information system according to the invention for forming individualised and/or optimal nutrition and/or medical information. The information unit 303 or at least part of the information unit 303 and the database and/or software used by it can be downloaded to the data terminal equipment 100, 206, 712-728 of the parties, for example, by a program from some information network, or it can be delivered using means intended for data transmission known by one skilled in the art, for example, on CD ROM or DVD disc. Especially to the nutrition dispenser 100, which is not provided with fixed data transmission connections, downloading can be performed via a mobile station network.

In addition, the information unit 303 typically comprises the memory equipment 732 and the equipment 734 for processing and analysing the information and for forming individualised optimal nutrition and/or medical information. The information unit 303 advantageously uses fuzzy logic for analysing information in the database equipment and for forming individualised nutrition information and/or medical information with the help of the analysed information. The nutrition unit 303 can handle and process information using the equipment 708, 732 and 734, for example, with the help of the Websom method utilising the self-organising map (SOM). In addition, the nutrition unit 303 can also define the reference profile of different parties or elements, such as the user's reference profile, with the help of the equipment 708, 732 and 734.

The information unit 303 can further comprise the equipment 736 for identifying the user, for example, with the help of the user ID and password. The user can also be identified with the identifier of the user's mobile station, such as mobile phone number.

In addition, the information unit 303 typically comprises the equipment 738 for delivering the formed nutrition information and/or medical information to at least one of the following: the nutrition dispenser 100, the producer 712, the quality control unit 714, the medical personnel unit 715, the scientific research unit 716, the shop system 718, the restaurant system 720, or some system of the user, such as the computer 722, the mobile station 206, the PDA device 206, and the digital television 206. The individualised optimal nutrition and/or medical information can also be delivered by letter or fax and, additionally, by dictating on the phone.

It has to be noted that the information to be stored to the database equipment and the data terminal equipment 100, 206, 712-728 of the parties, especially to the mobile stations 206, can be derived information, which as such does not reveal possibly delicate information about the individual, even when uncovered, but it expressly supports the process concerning the selection of nutrition.

Further, it has to be noted that, according to one embodiment, the user can use the nutrition dispenser 100 so that the equipment 630 of the nutrition dispenser 100 identify the user with the help of the equipment 630 in his data terminal equipment 206. The user's information essential for the information system can preferably be integrated to the equipment 630 of the data terminal equipment 206. In this case, the nutrition dispenser 100 can read the user's information, for example, via an infrared or radio link, for example, the Bluetooth link 710, from the user's data terminal equipment 206. After having read the information, the nutrition dispenser 100 can send the information to the information unit 303 of the information system, in which case the information unit can optimise the dose of nutrition and/or medication optimal for the user on the basis of its information. In addition, the nutrition dispenser 100 can deliver also the information about the dose intended to be prepared of prepared for the user to the information unit 303 of the information system.

According to one embodiment of the invention, the nutrition dispenser 100 can be arranged so that the information about the user's dose of nutrition and/or medication is delivered to the user, in which case the user can confirm the purchases he has made. For example, the user can delete part of the information or add some additional information or accept the delivered information. The information is preferably delivered to the user's data terminal equipment, such as mobile station, PDA device, digital television or computer, for example, as an SMS message or e-mail. Alternatively, the information can also be delivered to the user's service page in the Internet.

FIG. 8 is a flowchart of a method 800 for producing a dose of nutrition and/or medication suitable for the user with the help of the nutrition dispenser in accordance with the invention. In step 802, the user feeds his information to the nutrition dispenser, for example, with the help of the user interface of the nutrition dispenser, smart card or magnetic card, or a data processing device utilising short-range radio lin, such as a Bluetooth compatible data processing device. The information fed by the user can either be detailed information about the user (age, gender, nutrition and/or medical substance limitations, at least part of the user's genetic map), about the user's sports performance (energy consumption, duration, level of difficulty), or similar, or answers to questions asked by the nutrition dispenser. The information can comprise, for example, also the user ID and password, after which the nutrition dispenser can contact the information system in step 804 and the user's database for processing the user's information. However, the step 804 is optional.

After having fed the information and/or after having retrieved it from the database, the nutrients and/or medical substances suitable for the user, their amounts and proportions are determined in step 806 either with the help of the database arrangement 500 of the information system or with the equipment of the nutrition dispenser. In step 808, the suggestion can be presented to the user and, if the user accepts the dose of nutrition and/or medication and the nutrients and/or medical substances in it, their amounts and proportions suggested in step 810, the substances are measured out in step 812. If the user does not accept the suggestion, he can change the nutrients and/or medical substances, their amounts and proportions contained in the suggestion in step 814, after which it is possible to return back to step 806 or, alternatively, also to some other step. The substances measured out in step 816 are mixed with a mixer and served to the user in a form ready to be consumed. As the user accepts the suggestion, he can also be charged according to the methods mentioned above. Alternatively, charging can also be performed in connection of some other step. In addition, as the user accepts the suggestion, the information about the dose to be prepared for the user can be delivered to the information system.

Only some embodiments of the solution according to the invention have been presented above. The principle of the invention can naturally be varied within the scope of the patent claims, for example, for the part of the realisation and the areas of use. It has to be noted that the nutrition dispensers according to the invention and their properties disclosed in the examples and figures can be combined in different ways. The method can especially be applied to the manufacture of personified doses of nutrition and/or medication to people but, however, the invention is not restricted to this, but the invention can also be applied to the manufacture of doses of nutrition intended for other animals, such as domestic animals and cattle.

It still has to be noted that, besides personified optimal dose of nutrition, also an optimal dose of medication can be prepared for the user with the help of the invention. According to one embodiment of the invention, with the invention it is possible to prepare a dose of nutrition and/or medication optimal for the user, for example, according to components so that the effect of nutrients and/or other medical substances on the concentrations, absorption and effect of a medical substance and/or nutrient and/or also of some other medical substances and/or nutrients and on the user's metabolism are taken into account.

The data transmission connections disclosed above can be any data transmission connections known to one skilled in the art. Especially, the nutrition dispenser can be compatible with at least one of the following data transmission specifications: TCP/IP, CDMA, GSM, HSCSD, GPRS, WCDMA, EDGE, Bluetooth, UMTS, Teldesic, Iridium, Inmarsat, WLAN, DIGI-TV, ISDN, xDSL, RPC, Home-Pna, and imode. In addition, the nutrition dispenser can comprise at least one of the following operating systems for performing the FPC program of the invention: Unix, MS-windows, EPOC, NT, MSCE, Linux, PalmOS, and GEOS.

The invention claimed is:

1. A dispenser (100) for defining and preparing an optimal dose of nutrition, medication or cosmetic personalized for a user, comprising:
   a user interface (102) configured for feeding in information about the user;
   an equipment (106) connected to the user interface, the equipment configured to define an optimal dose, personalized for the user, of at least one of a nutrition, a medication and a cosmetic;
   a telecommunication connection (306) for connecting the equipment (106) to a database (304) storing i) user information, ii) information of the user's genetic background, and iii) information about at least one of nutrients and medical substances;
   rooms (108) preserving at least two substances, the substances being at least one of the nutrients and the medical substances; and
   a dosing device (110) connected to the rooms (108) and to the equipment (106), and configured to measure out an amount of the substances preserved in the rooms, wherein,
   the stored user information, the user's genetic background information, and the information about at least one of the nutrients and the medical substances are communicated from the database (304) through the telecommunication connection (306) to the equipment (106),
   the equipment (106) defines the optimal dose based on the fed-in user information together with the the stored user information, the user's genetic background information, and the information about the at least one of the nutrients and the medical substances communicated from the database (304) through the telecommunication connection (306) to the equipment (106), and
   the dosing device (110) measures out the substances preserved in the rooms (108) to prepare the optimal dose as defined by the equipment (106).

2. The dispenser according to claim 1, wherein, the user's genetic background information stored in the database comprises genetic map information about the user including information concerning genes of the user, the user gene information being based on genetic tests made to the user.

3. The dispenser according to claim 1, wherein,
   the rooms (108) are containers that are air-tight, moisture-proof, and one of cooled and heated, and
   the equipment (106) comprises an information system utilizing fuzzy logic.

4. The dispenser of claim 1, wherein,
   the user information comprises the user's age, gender, nutrient limitations, medical substance limitations, allergy informations, and environmental information,
   the environmental information includes temperature, energy consumption, sports the user participates in, a level of difficulty for each sport, and a duration of performance for each sport, the user interface (102) is configured for the user to input at least some of the user information responsive to questions presented to the user, and the questions presented to the user include information identifying a suggested dose to be prepared for the user and whether the user accepts the suggested dose.

5. The dispenser according to claim 1, wherein the database (304) comprises information selected from the group consisting of:
   at least one probability weighting coefficient for at least one gene influencing at least one health property specific to the user with a certain probability;
   at least one probability weighting coefficient for at least one of a nutrient and a medical substance influencing at least one health property in a healing or harmful manner with regard to the user with a certain probability;
   at least one probability weighting coefficient for at least one gene together with at least one of a nutrient and a medical substance influencing at least one health property in a healing or harmful manner with regard to the user with a certain probability;
   at least one probability weighting coefficient for the user being allergic to at least one of a nutrient and a medical substance with a certain probability;
   an optimal quantity proportion of at least two substances selected from the group consisting of nutrients, medical substances and combinations thereof;
   information which at least one foodstuff has at least one nutrient in the database (304).

6. The dispenser according to claim 1, wherein the equipment (116) receives information from the database (304) to perform at least one of:
   comparing at least one gene from the genetic map of the user with genetic map information, which includes the gene, in and the database (304), selecting a probability weighting coefficient between the gene and at least one health property influenced by the gene;
   selecting a probability weighting coefficient between at least one health property and at least one of a nutrient and a medical substance, which influences the health property either in a healing or harmful manner with regard to the user with a certain probability;
   forming information describing the suitability of at least one of a nutrient and a medical substance for the user with the help of a probability weighting coefficients;
   arranging substances, each substance being one of a nutrient and a medical substance, influencing at least one health property in a healing or harmful manner with regard to the user with a certain probability, and probabilities related to the substances being used for the optimal dose when defining information describing the suitability of the substances for the user to such an order that the substance with the highest probability to have a healing effect on the health property is placed as the most important, and delivering the information of the substances to the equipment (106);
   registering the amounts of at least one of a nutrient and a medical substance consumed by the user in a cumulative manner and so that the at least one of a nutrient and medical substance consumed can be connected with the user's identifier information;
   calculating the combination of at least two probability weighting coefficients between substances selected from the group consisting of nutrients, medical substances, and mixtures thereof and health properties from different genes of the database (304), the genes also present in the user, the value of the combination being closest to the best value, and forming a dose comprising the substances best suitable for the user by picking the information about the substances, to which the probability weighting coefficients are related, with which the best value was formed, and delivering the information about the substances to the nutrition dispenser;
   comparing the cumulative amounts of a substances selected from the group consisting of nutrients, medical substances, and mixtures thereof consumed by the users within the selected period of time with the intake limits set for the substances, selecting at least one substance, the cumulative amount of which in the period of time is below the area of the defined intake limit, and if the value of the probability weighting coefficient for the substance influencing a certain health property in a healing manner is above the predetermined limit, suggesting the substance to be added to the dose of substance to be produced for the user.

7. The dispenser according to claim 1, wherein the database (304) is a distributed database (304) so that at least one first part of the database (304) is located in at least one first data processing equipment and at least one second part of the database (304) is located in at least one second data processing equipment.

8. The dispenser according to claim 1, wherein the database (304) comprises at least one piece of information selected from the group consisting of:
   information related to the relations between illnesses and nutrition/genes characteristic of reference groups of the user,
   information about medical substances and the effects on the change in the state of illnesses and the change in the metabolic and nutritive and/or medical state,
   information concerning the environment of reference groups,
   information related to the state of health of the user and the structure and/or functional state of the genes of the user,
   information related to the environment of the user, information related to the physical performances performed by the user, information related to the factors caused by the growth environment of the nutrition intended to for the user, and
   information related to the manufacturing method of at least one dose of nutrition, medication and/or cosmetic intended for the user, the amount and time of consuming.

9. The dispenser according to claim 1, wherein each of the at least two substances is selected from the group consisting of a raw material, a semi-processed product, a processed product, a synthetically manufactured nutrient and/or medical substance, and combinations thereof.

10. The dispenser according to claim 1, wherein each of the at least two substances is, individually, in a form selected from the group consisting of liquid, concentrate, powder, emulsion, tablet, capsule, pill, granule and pieces of ice.

11. The dispenser according to claim 1, wherein at least one of the substances preserved in the rooms (108) is selected from the group consisting of: water, flavour substance, vitamin, micronutrients, fibre, flavonoids, amino acids, protein, sugar, mineral, lycopen, carbohydrates, fat, minerals, substances containing scent, components of green tea, glucose, fructose, caffeine, guarana, green tea extract, pygnogenol, betaine, methylen-suiphonyl-methane (MSM), magnesium, potassium, chrome, carnitine, taurine, conroitine sulphate, glucose aminoglycanes, curcuma, antibodies, probiotics, prebiotics, herbs, passionflower, hop, oat sprout, lemon balm, and ethereal oils.

12. The dispenser according to claim 1, wherein,
the user interface comprises at least one device selected from the group consisting of: keyboard (102), control stick, a user interface utilising short-range radio link, a user interface utilising smart cards (208), a user interface utilising magnet cards, and
further comprising a printing equipment which may include a display (104) and a printer (212).

13. The dispenser according to claim 1, wherein the equipment (106) is configured to accept and, when defining the optimal dose, process as part of the fed-in user information each of: name, ID information, age, gender, length, weight, allergy, liking, special diet, at least part of the genetic map, information about genetic background and structure, genotype (DNA), functional state of genes, tribe, group, nationality, illnesses, mental state, medication, living environment, working environment, type of work, family relations, individual history, work or sports performance, fat percentage, muscular mass, water mass, blood pressure, blood sugar, hemoglobin, cholesterol, locomotoric illness, depression, cardiac disease, hypertension, asthma, headache, migraine, mental illness, illnesses caused by alcohol, dementia, and hormone-dependent cancer.

14. The dispenser according to claim 1, configured to accept and, in defining the optimal dose, process performance and fitness information from a fitness device (402) used by the user, the performance and fitness information being accepted from a source selected from the group consisting of: a telecommunications connection, a magnetic card, a smart card, a printed code, and a short-range radio link.

15. The dispenser, according to claim 1, wherein, the defined optimal dose is communicated from the equipment via a short-range radio link to a mobile station of the user, via a smart card read/write equipment to a smart card of the user, via a magnetic card read/write equipment to a magnetic card of the user, and via the telecommunication connection to the database (304).

16. The dispenser according to claim 1, further comprising:
a mixer (112) for mixing the substances to a finished optimal dose of nutrition, medication or cosmetic and into a form dispensed to the user.

17. A system (700) for producing a dose of nutrition, medication or cosmetic, comprising:
a nutrition dispenser (100) configured to produce a dose of nutrition, medication or cosmetic;
a database (304) comprising i) stored user information, ii) user genetic background information, and iii) information about at least one of nutrients and medical substances;
an information system (303) comprising memory equipment and configured to process and analyze the stored user information, the user genetic background information, and the information about the at least one of nutrients and medical substances from the database (304) so as to define an optimal dose of nutrition, medication or cosmetic for the user;
data transmission connections (706, 710) connecting the database (304) and the nutritional dispenser (100) to the information system (303), wherein,
the information system (303) defines the optimal dose of nutrition, medication or cosmetic for the user based, in part, on the user genetic background information from the database (304), and
the nutrition dispenser (100) measures out nutrient and/or medical substances to produce the defined optimal dose of nutrition, medication or cosmetic personalized to the user.

18. A method for producing an optimal dose of nutrition, medication or cosmetic for a user with a nutrition dispenser, comprising:
entering information about a user into a user interface, wherein the information is entered by one of i) the user for which the optimal dose is produced and ii) a person other than the user;
defining an optimal dose of nutrition, medication or cosmetic for the user, including defining amounts and proportions of substances, the substances being at least one of nutrients and medical substances, the defined optimal dose being based on at least the information entered about the user, the user's genetic background information, and information about substances for nutritions, medications or cosmetics; and
measuring out the defined amounts and proportions of the substances from a nutrition dispenser.

19. The method according to claim 18, further comprising:
mixing the measured defined substances in the nutrition dispenser to form a finished optimal dose of nutrition, medication or cosmetic for dispensing; and
dispensing the optimal dose of nutrition, medication or cosmetic from the nutrition dispenser into a serving dish or bottle.

20. A dispenser (100) of claim 1, further comprising:
a housing that houses the user interface (102), the rooms (108), the dosing device (11), and the telecommunication connection (306),
wherein, each of the database (304) and the equipment (106) is, individually, one of housed by the housing and operatively connected to the housing.

* * * * *